US012440204B2

(12) United States Patent
Shuey et al.

(10) Patent No.: US 12,440,204 B2
(45) Date of Patent: Oct. 14, 2025

(54) MEDICAL DEVICE FOR CUTTING A SUTURE DURING A MINIMALLY INVASIVE PROCEDURE

(71) Applicant: BOSTON SCIENTIFIC SCIMED, INC., Maple Grove, MN (US)

(72) Inventors: Daniel Shuey, Pine City, MN (US); Christopher J. Koudela, New London, MN (US); Aaron Abbott, Columbia Heights, MN (US); Mitchell Nelson, Hudson, WI (US); Joel T. Eggert, Plymouth, MN (US); James K. Cawthra, Jr., Elk River, MN (US); Sandra L. Weeda, Osceola, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 138 days.

(21) Appl. No.: 18/529,101

(22) Filed: Dec. 5, 2023

(65) Prior Publication Data

US 2024/0180546 A1 Jun. 6, 2024

Related U.S. Application Data

(60) Provisional application No. 63/430,470, filed on Dec. 6, 2022.

(51) Int. Cl.
*A61B 17/04* (2006.01)
*A61B 17/00* (2006.01)

(52) U.S. Cl.
CPC ...... *A61B 17/0467* (2013.01); *A61B 17/0469* (2013.01); *A61B 2017/00367* (2013.01);
(Continued)

(58) Field of Classification Search
CPC ............ A61B 17/0467; A61B 17/0469; A61B 2017/00367; A61B 2017/0042; A61B 2217/005; A61B 2217/007
See application file for complete search history.

(56) References Cited

U.S. PATENT DOCUMENTS 5,133,723 A 7/1992 Li et al.
5,702,397 A 12/1997 Goble et al.
(Continued)

FOREIGN PATENT DOCUMENTS

CN 109223064 A 1/2019
EP 2775896 A2 9/2014
(Continued)

OTHER PUBLICATIONS

International Search Report and Written Opinion for the International Application No. PCT/US2020/040678, mailed Oct. 16, 2020, 10 pages.
(Continued)

*Primary Examiner* — Phong Son H Dang
(74) *Attorney, Agent, or Firm* — Seager, Tufte & Wickhem, LLP

(57) ABSTRACT

A medical device for cutting a suture during a minimally invasive procedure includes an elongate shaft, a handle housing disposed at the proximal end of the elongate shaft, and a cutting blade disposed proximate the distal end of the elongate shaft. A proximal portion of the handle housing includes an actuation mechanism including a lever arm having a first portion disposed outside of the handle housing and extending distally from the proximal portion of the handle housing. Translation of the first portion of the lever arm relative to the handle housing axially translates the cutting blade within the elongate shaft. A medical device system may include a stand configured to support at least
(Continued)

one medical device and a medical device securable to the stand.

17 Claims, 15 Drawing Sheets

(52) U.S. Cl.
CPC . *A61B 2017/0042* (2013.01); *A61B 2217/005* (2013.01); *A61B 2217/007* (2013.01)

(56) References Cited

U.S. PATENT DOCUMENTS 6,183,463 B1 2/2001 Webster, Jr.
7,235,086 B2 * 6/2007 Sauer .................... A61B 1/0014 606/151
7,736,388 B2 6/2010 Goldfarb et al.
8,109,945 B2 2/2012 Boehlke
8,252,050 B2 8/2012 Maisano et al.
8,303,622 B2 11/2012 Alkhatib
8,777,968 B2 7/2014 Evans et al.
8,852,088 B2 10/2014 Ransden et al.
9,180,005 B1 11/2015 Lashinski
9,192,471 B2 11/2015 Bolling
9,572,667 B2 2/2017 Solem
9,592,048 B2 * 3/2017 Moehle .................. A61F 2/2448
9,610,156 B2 4/2017 Lashinski
9,622,862 B2 4/2017 Lashinski et al.
9,681,864 B1 6/2017 Gammie et al.
9,795,480 B2 10/2017 Bolling et al.
9,848,983 B2 12/2017 Lashinski et al.
9,980,719 B2 5/2018 Tegels
10,136,993 B1 11/2018 Metchik et al.
10,179,236 B2 1/2019 Haasl et al.
10,278,852 B2 5/2019 Griffin
10,321,999 B2 6/2019 Glenn et al.
10,335,275 B2 7/2019 Lashinski et al.
10,433,962 B2 10/2019 Rafiee et al.
10,478,629 B2 11/2019 An et al.
10,548,731 B2 2/2020 Lashinski et al.
10,555,813 B2 2/2020 Lashinski et al.
10,667,804 B2 6/2020 Basude et al.
10,667,815 B2 6/2020 Krone et al.
10,799,356 B2 10/2020 McAfee et al.
10,945,718 B2 3/2021 Hiorth et al.
11,219,447 B2 * 1/2022 Juan .................... A61B 17/0485
11,553,909 B2 * 1/2023 Gilbert ................ A61B 17/0487
11,660,118 B1 * 5/2023 Kusumoto ............. A61N 1/362 606/129
2003/0167062 A1 * 9/2003 Gambale ............ A61B 17/0487 606/148
2004/0088003 A1 5/2004 Leung et al.
2004/0167539 A1 8/2004 Kuehn et al.
2004/0230280 A1 11/2004 Cates et al.
2006/0207607 A1 9/2006 Hirotsuka et al.
2006/0276890 A1 12/2006 Solem et al.
2007/0010829 A1 * 1/2007 Nobles ............... A61B 17/0491 606/148
2007/0080188 A1 4/2007 Spence et al.
2007/0118151 A1 5/2007 Davidson
2008/0051863 A1 2/2008 Schneider et al.
2008/0195126 A1 8/2008 Solem
2008/0228267 A1 9/2008 Spence et al.
2008/0234729 A1 * 9/2008 Page .................. A61B 17/0487 606/232
2009/0105729 A1 4/2009 Zentgraf
2010/0094314 A1 4/2010 Hernlund et al.
2010/0249920 A1 9/2010 Bolling et al.
2011/0060407 A1 3/2011 Ketai et al.
2011/0301699 A1 12/2011 Saadat
2012/0130492 A1 5/2012 Eggli et al.
2012/0172892 A1 7/2012 Grubac et al.
2012/0184991 A1 7/2012 Paraschac et al.
2013/0035757 A1 2/2013 Zentgraf et al.
2013/0085562 A1 4/2013 Rincon et al.
2013/0096611 A1 4/2013 Sullivan
2013/0110230 A1 5/2013 Solem
2014/0046347 A1 2/2014 Cully et al.
2014/0276979 A1 9/2014 Sauer et al.
2015/0250590 A1 9/2015 Gries et al.
2017/0135816 A1 5/2017 Lashinski et al.
2017/0245993 A1 8/2017 Gross et al.
2017/0252032 A1 9/2017 Hiorth et al.
2018/0185153 A1 7/2018 Bishop et al.
2018/0250133 A1 9/2018 Reich et al.
2018/0296327 A1 10/2018 Dixon et al.
2018/0303614 A1 10/2018 Schaffner et al.
2019/0206565 A1 7/2019 Shelton, IV
2019/0314634 A1 10/2019 Deininger et al.
2019/0343634 A1 11/2019 Garvin et al.
2019/0358037 A1 11/2019 McAfee et al.
2020/0163768 A1 5/2020 Apkarian et al.
2020/0261699 A1 8/2020 Rizq et al.
2021/0000597 A1 1/2021 Shuey et al.
2021/0000598 A1 1/2021 Shuey et al.
2021/0000599 A1 1/2021 Shuey et al.
2021/0007847 A1 1/2021 Eggert et al.
2021/0068840 A1 3/2021 Allen, IV et al.
2021/0068955 A1 3/2021 Bruner
2021/0106422 A1 4/2021 Rajagopal et al.
2021/0128140 A1 5/2021 Wales et al.
2021/0128141 A1 5/2021 Deuel et al.
2022/0015904 A1 1/2022 Hiorth et al.
2022/0015906 A1 1/2022 Hiorth et al.
2022/0022863 A1 1/2022 Hiorth et al.
2022/0031303 A1 2/2022 Yarra et al.
2022/0096235 A1 3/2022 Giese et al.
2022/0192830 A1 6/2022 Schneider et al.
2023/0011214 A1 1/2023 Nelson et al.
2023/0062599 A1 3/2023 Walker et al.
2023/0121477 A1 * 4/2023 Tschudy ............... G04G 13/026 368/73
2023/0123832 A1 4/2023 Abbott et al.
2023/0149170 A1 5/2023 Giese et al.
2023/0149685 A1 5/2023 Giese et al.
2023/0414215 A1 * 12/2023 Carpenter .......... A61B 17/0483
2024/0225641 A1 * 7/2024 Wang ................... A61B 17/072
2025/0169817 A1 * 5/2025 Shelton, IV ........... G16H 40/60

FOREIGN PATENT DOCUMENTS

EP 2626012 B1 9/2015
EP 3100761 A1 12/2016
EP 3104772 B1 3/2019
EP 3881755 A1 9/2021
GB 2579420 A 6/2020
WO 2008112740 A2 9/2008
WO 2013069019 A1 5/2013
WO 2015193728 A2 12/2015
WO 2018013856 A1 1/2018
WO 2019186500 A2 10/2019
WO 2020012481 A2 1/2020
WO 2020109596 A1 6/2020
WO 2020123719 A1 6/2020
WO 2021003372 A1 1/2021
WO 2021003375 A1 1/2021
WO 2021003387 A1 1/2021
WO 2021011206 A2 1/2021
WO 2021076056 A1 4/2021
WO 2021080782 A1 4/2021
WO 2021086903 A1 5/2021
WO 2022053896 A1 3/2022
WO 2022074473 A1 4/2022
WO 2022074478 A1 4/2022
WO 2022106497 A1 5/2022

OTHER PUBLICATIONS

International Search Report and Written Opinion for the International Patent Application No. PCT/US2020/040672, mailed Oct. 16, 2020.

(56) References Cited

OTHER PUBLICATIONS

"Fish Fighter® Kwik-Pull™ Anchor Retriever" Fish Fighter Products, 6 pages, URL: https://fishfighterproducts.com/shop/fish-fighter-kwik-pull-anchor-retriever/ Retrieved Aug. 29, 2020.
"Knotless SutureTak® Anchor" Arthrex, 2 pages, 1 page, URL: https://www.arthrex.com/resources/animation/2d7_OmxWw0edpgFLMMbz5A/knotless-suturetak-anchor. Retrieved Aug. 29, 2020.
"Shoulder Labral Repair with Knotless SutureTak® Anchor" Arthrex, retrieved Aug. 29, 2020, URL: https://www.arthrex.com/resources/animation/9cpCPTZLCEGvYQFMdlKwxg/shoulder-labral-repair-with-knotless-suturetak-anchor 7 pages. Retrieved Aug. 29, 2020.
"Knotless SutureTak Anchor Instability Repair" Arthrex, 6 pages, Mar. 1, 2018.
APS—Annapolis Performance Sailing., "Ronstan Constrictor Rope Clutch| Expert Review"—YouTube, 3 pages. Retrieved Oct. 9, 2020.
International Search Report and Written Opinion for the International Patent Application No. PCT/US2021/051722, mailed Jan. 7, 2022, 10 pages.
Invitation to Pay Additional Fees and where Applicable Protest Fees, for International Application No. PCT/aaUS2022/042098, date of mailing, Dec. 2, 2022. (13 pages).
International Search Report and Written Opinion dated Dec. 8, 2022 for International Application No. PCT/US2022/042079.
International Search Report and Written Opinion for International Application No. PCT/US2022/042085, date of mailing Dec. 5, 2022. (11 pages).
Invitation to Pay Additional Fees dated Oct. 6, 2023 for International Application No. PCT/US20213/025682.
Boston Scientific Invention Disclosure Submission Form IDF 21-D0271, 7 pages, 2021.
Boston Scientific, Saline Antechamber for Wet to Wet Catheter Introduction, Disclosure No. 21-D027, 9 pages, 2021.
Boston Scientific IDF 21-D027, Drawings, 4 pages, Nov. 16, 2021.
Invitation to Pay Additional Fees dated Jan. 3, 2023 for International Application No. PCT/US2022/044858.
International Search Report and Written Opinion dated Sep. 18, 2023 for International Application No. PCT/US2023/025679.
International Search Report and Written Opinion dated Nov. 22, 2023 for International Application No. PCT/US2023/025683.
International Search Report and Written Opinion dated Mar. 12, 2024 for International Application No. PCT/US2023/082512.

* cited by examiner

MEDICAL DEVICE FOR CUTTING A SUTURE DURING A MINIMALLY INVASIVE PROCEDURE

CROSS-REFERENCE TO RELATED APPLICATIONS

This application claims the benefit of priority of U.S. Provisional Application No. 63/430,470 filed Dec. 6, 2022, the entire disclosure of which is hereby incorporated by reference.

TECHNICAL FIELD

The present disclosure pertains to medical devices and methods for using medical devices. More particularly, the present disclosure pertains to aspects of medical devices for cutting a suture during a minimally invasive procedure such chordae repair.

BACKGROUND

A wide variety of intracorporeal medical devices have been developed for medical use, for example, surgical and/or intravascular use. These medical devices are manufactured by any one of a variety of different manufacturing methods and may be used according to any one of a variety of methods. There is an ongoing need to provide alternative medical devices as well as alternative methods for manufacturing and/or using medical devices.

SUMMARY

In one example, a medical device for cutting a suture during a minimally invasive procedure may comprise an elongate shaft having a proximal end, a distal end, and a central longitudinal axis extending from the proximal end to the distal end, a handle housing disposed at the proximal end of the elongate shaft, and a cutting blade disposed proximate the distal end of the elongate shaft. A proximal portion of the handle housing may include an actuation mechanism including a lever arm having a first portion disposed outside of the handle housing and extending distally from the proximal portion of the handle housing. Translation of the first portion of the lever arm relative to the handle housing may axially translate the cutting blade within the elongate shaft.

In addition or alternatively to any example described herein, the actuation mechanism includes a rack axially slidable parallel to the central longitudinal axis and at least one gear engaged with the rack.

In addition or alternatively to any example described herein, a second portion of the lever arm disposed inside of the handle housing is coupled to the at least one gear.

In addition or alternatively to any example described herein, the at least one gear includes a semi-circular profile.

In addition or alternatively to any example described herein, the cutting blade is operably coupled to the rack.

In addition or alternatively to any example described herein, translation of the first portion of the lever arm away from the handle housing axially translates the rack within the handle housing.

In addition or alternatively to any example described herein, translation of the first portion of the lever arm away from the handle housing axially translates the rack proximally within the handle housing.

In addition or alternatively to any example described herein, the medical device may comprise a locking element configured to prevent movement of the lever arm relative to the handle housing.

In addition or alternatively to any example described herein, a medical device system may comprise a stand configured to support at least one medical device, and a medical device securable to the stand. The medical device may comprise an elongate shaft having a proximal end, a distal end, and a central longitudinal axis extending from the proximal end to the distal end, a handle housing disposed at the proximal end of the elongate shaft, and a cutting blade disposed proximate the distal end of the elongate shaft. A proximal portion of the handle housing may include an actuation mechanism including a lever arm having a first portion disposed outside of the handle housing and extending distally from the proximal portion of the handle housing. Translation of the first portion of the lever arm relative to the handle housing may axially translate the cutting blade within the elongate shaft.

In addition or alternatively to any example described herein, the stand includes a support member having a first yoke configured to engage the handle housing and a second yoke configured to engage the handle housing.

In addition or alternatively to any example described herein, the handle housing includes a first groove configured to engage the first yoke and a second groove configured to engage the second yoke.

In addition or alternatively to any example described herein, the support member includes at least one locking element configured to secure the handle housing to the support member.

In addition or alternatively to any example described herein, the stand includes a second support member configured to engage a steering system having a steerable flexible tubular elongate member extending away from the second support member, the steering system being configured to receive the elongate shaft of the medical device within the steerable flexible tubular elongate member.

In addition or alternatively to any example described herein, the second support member includes a first yoke configured to engage a handle of the steering system and a second yoke configured to engage the handle of the steering system.

In addition or alternatively to any example described herein, a medical device for cutting a suture during a minimally invasive procedure may comprise an elongate shaft having a proximal end, a distal end, and a central longitudinal axis extending from the proximal end to the distal end, a handle housing disposed at the proximal end of the elongate shaft, and a cutting blade disposed proximate the distal end of the elongate shaft. A proximal portion of the handle housing may include an actuation mechanism configured to translate the cutting blade within the elongate shaft. The actuation mechanism may include a rack disposed within the handle housing, wherein the rack is axially slidable parallel to the central longitudinal axis, and a lever arm having a first portion disposed outside of the handle housing and a second portion disposed inside of the handle housing, wherein the second portion includes a first leg fixedly attached to a first gear configured to engage the rack and a second leg fixedly attached to a second gear configured to engage the rack.

In addition or alternatively to any example described herein, translation of the first portion of the lever arm relative to the handle housing axially translates the rack within the handle housing.

In addition or alternatively to any example described herein, a pull wire extends from the rack to the cutting blade.

In addition or alternatively to any example described herein, the first leg and the second leg are disposed radially outward from the rack relative to the central longitudinal axis.

In addition or alternatively to any example described herein, the first leg and the second leg are disposed on opposite sides of the rack.

In addition or alternatively to any example described herein, a distal portion of the handle housing includes one or more ports in fluid communication with the elongate shaft.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description in connection with the accompanying drawings, in which.

Figure 1:
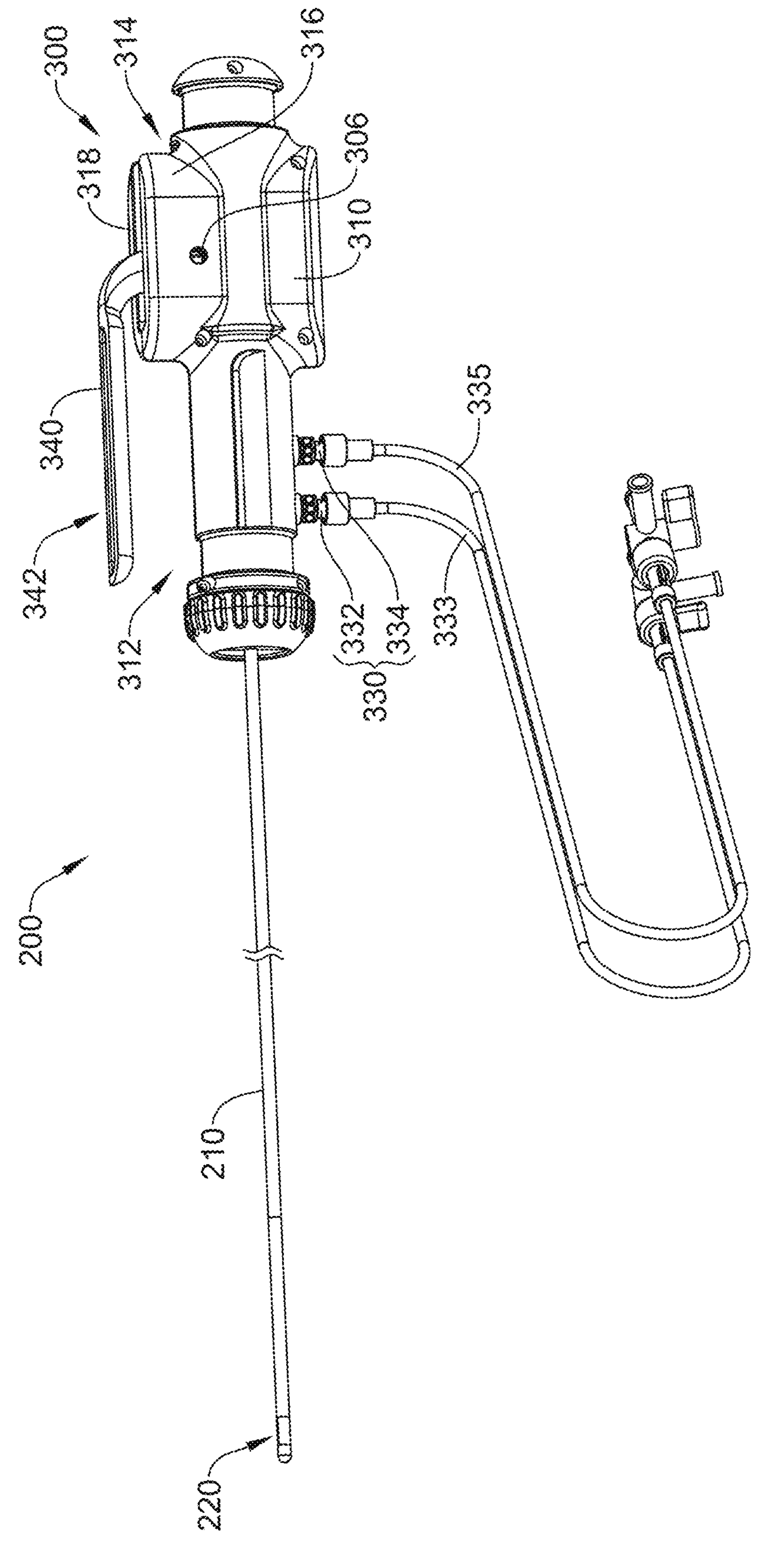
FIGS. 1-3 illustrate selected aspects of a medical device associated with the disclosure.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the disclosure. Those skilled in the art will recognize that the various elements described and/or shown may be arranged in various combinations and configurations without departing from the scope of the disclosure. The detailed description and drawings illustrate example embodiments of the disclosure.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean the greatest measurement of a stated or identified dimension, unless the extent or dimension in question is preceded by or identified as a "minimum", which may be understood to mean the smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete structures or elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to implement the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Diseases and/or medical conditions that impact the cardiovascular system are prevalent throughout the world. Some mammalian hearts (e.g., human, etc.) include four heart valves: a tricuspid valve, a pulmonary valve, an aortic valve, and a mitral valve. The purpose of the heart valves is to control blood flow into the heart from major veins (e.g., the inferior vena cava, the superior vena cava, etc.), through the heart (from atria to ventricles), and out of the heart into the major arteries connected to the heart (e.g., the aorta, the pulmonary artery, etc.). Each heart valve may have a plurality of valve leaflets configured to shift between an open configuration permitting fluid flow through the heart valve and a closed configuration wherein free edges of the valve leaflets coapt to substantially prevent fluid flow through the heart valve. The heart may include a left atrium, a left ventricle, a right atrium, and a right ventricle. The left ventricle may include a first papillary muscle attached to and/or extending from a wall of the left ventricle, a second papillary muscle attached to and/or extending from the wall of the left ventricle, and a plurality of chordae tendineae connecting the first papillary muscle and the second papillary muscle to the plurality of leaflets of the mitral valve. In a normally functioning heart valve, blood is permitted to pass or flow downstream through the heart valve (e.g., from an atrium to a ventricle, from a ventricle to an artery, etc.) when the heart valve is open (e.g., during diastole), and when the heart valve is closed (e.g., during systole), blood is prevented from passing or flowing back upstream through the heart valve (e.g., from a ventricle to an atrium, etc.).

In some instances, when mitral regurgitation occurs, the mitral valve fails to open and/or close properly such that blood is permitted to pass or flow back upstream through the mitral valve. In some cases, the defective heart valve may have leaflets that may not close, or may not be capable of closing, completely. In some instances, secondary or functional mitral regurgitation may be a secondary effect of left ventricular dysfunction, where left ventricular dilatation and/or distension caused by ischemic or idiopathic cardiomyopathy, for example, results in annular dilatation and/or distension of the left ventricle and papillary muscle displacement with subsequent leaflet tethering and insufficient coaptation of the mitral leaflets during systole. In some instances, degenerative mitral regurgitation may involve redundant excessive tissue in part of the heart valve and/or the heart valve leaflets (e.g., mitral valve prolapse). In some instances, mitral regurgitation may be caused or exacerbated by stretching and/or rupture of one of more of the plurality of chordae tendineae.

Surgical methods of treating stretched or ruptured chordae tendineae may include replacing the chordae by sewing one or more sutures (e.g., Gore-Tex®, etc.) to the first papillary muscle and/or the second papillary muscle and to one or more leaflets of the plurality of valve leaflets to mimic the natural chordae tendineae. However, open heart cardiac surgery may carry significant risk to the patient, including complications, disability during recovery, and/or morbidity. Minimally invasive solutions may include transcatheter artificial valve replacement, but valve replacement surgeries may require lifelong anticoagulant treatment. Another alternative solution may involve edge-to-edge fixation of the plurality of leaflets, but such treatments prevent the option of minimally invasive valve replacement surgery in the future. As such, there is a need for minimally invasive treatments for repairing a heart valve while maintaining the option for future treatment options.

Disclosed herein are medical devices, systems, and/or methods that may be used to diagnose, treat, and/or repair a portion of the cardiovascular system. One possible remedy is a percutaneous procedure which may replace stretched and/or ruptured chordae tendineae. The disclosed medical devices, systems, and/or methods may preferably be used percutaneously via minimally invasive intravascular techniques, or in an alternative method, using open-heart surgical techniques. The medical devices, systems, and/or methods disclosed herein may also provide a number of additional desirable features and/or benefits as described in more detail below.

FIG. 1 illustrates selected aspects of a medical device 200 for cutting a suture 140 (e.g., FIGS. 3-4) during a minimally invasive procedure. In some embodiments, the medical device 200 may include an elongate shaft 210 having a proximal end, a distal end, and a central longitudinal axis extending from the proximal end to the distal end. In some embodiments, the medical device 200 and/or the elongate shaft 210 may include a distal tip member 220 fixedly attached to the distal end of the elongate shaft 210. In some embodiments, the distal tip member 220 may be integrally formed with the elongate shaft 210. In some embodiments, the distal tip member 220 may be constructed separately from the elongate shaft 210 and then fixedly attached to the elongate shaft 210. Some suitable but non-limiting materials for the elongate shaft 210 and/or the distal tip member 220, for example metallic materials, polymer materials, composite materials, etc., are described below.

In some embodiments, a cutting blade 260 may be disposed proximate the distal end of the elongate shaft 210. In some embodiments, the cutting blade 260 may be disposed within the distal tip member 220. Additional details related to the cutting blade 260 and/or the distal tip member 220 are described herein.

In some embodiments, the medical device 200 may include a handle 300 and/or a handle housing 310 disposed at the proximal end of the elongate shaft 210. The elongate shaft 210 may extend distally from the handle 300 and/or the handle housing 310. In at least some embodiments, the proximal end of the elongate shaft 210 may be fixedly attached to the handle housing 310. In some embodiments, the handle housing 310 may include an aperture 306 extending through a sidewall of the handle housing 310. Additional details and/or uses for the aperture 306 are described below.

In some embodiments, the handle 300 and/or the handle housing 310 may include one or more ports 330 attached to the handle housing 310 and in fluid communication with the elongate shaft 210. In some embodiments, the one or more ports 330 may include a first port 332 and a second port 334. In some embodiments, a fluid source may be connectable to the first port 332 via a first tube 333 and a vacuum source may be connectable to the second port 334 via a second tube 335, or vice versa. The fluid source may supply a fluid such as a saline solution or other biocompatible fluid into the elongate shaft 210 and the vacuum source may suction and/or remove air bubbles, debris, contamination, etc. from the elongate shaft 210. Other configurations are also contemplated. Some suitable but non-limiting materials for the handle 300, the handle housing 310, etc., for example metallic materials, polymer materials, composite materials, etc., are described below In some embodiments, the medical device 200 may be configured in a “side shooter” or single operator exchange (SOE) configuration. In the “side shooter” or single operator exchange (SOE) configuration, the suture 140 (e.g., FIGS. 3-4) may pass into a lumen of the medical device 200 at or near a distal end thereof and exit out a side of the medical device 200 and thereafter extend alongside the medical device 200. In some embodiments, the medical device 200 may be configured in an internal or over-the-wire (OTW) configuration. In the internal or over-the-wire (OTW) configuration, the suture 140 may pass into a lumen of the medical device 200 at or near the distal end thereof an extend internally an entire length of the medical device 200 to a proximal port or opening. Compared to the “side shooter” or single operator exchange (SOE) configuration, the internal or over-the-wire (OTW) configuration may require the suture 140 to have additional length to facilitate advancing the medical device 200 over the entire length of the suture 140. In the “side shooter” or single operator exchange (SOE) configuration, the suture 140 may be shorter because the medical device 200 only requires a short segment of the suture 140 to be passed through and/or inside of the medical device 200. For the purpose of illustration only, the medical device 200 is shown in the “side shooter” or single operator exchange (SOE) configuration herein, but such illustration shall not be deemed to limit the disclosure to the “side shooter” or single operator exchange (SOE) configuration.

Figure 2:
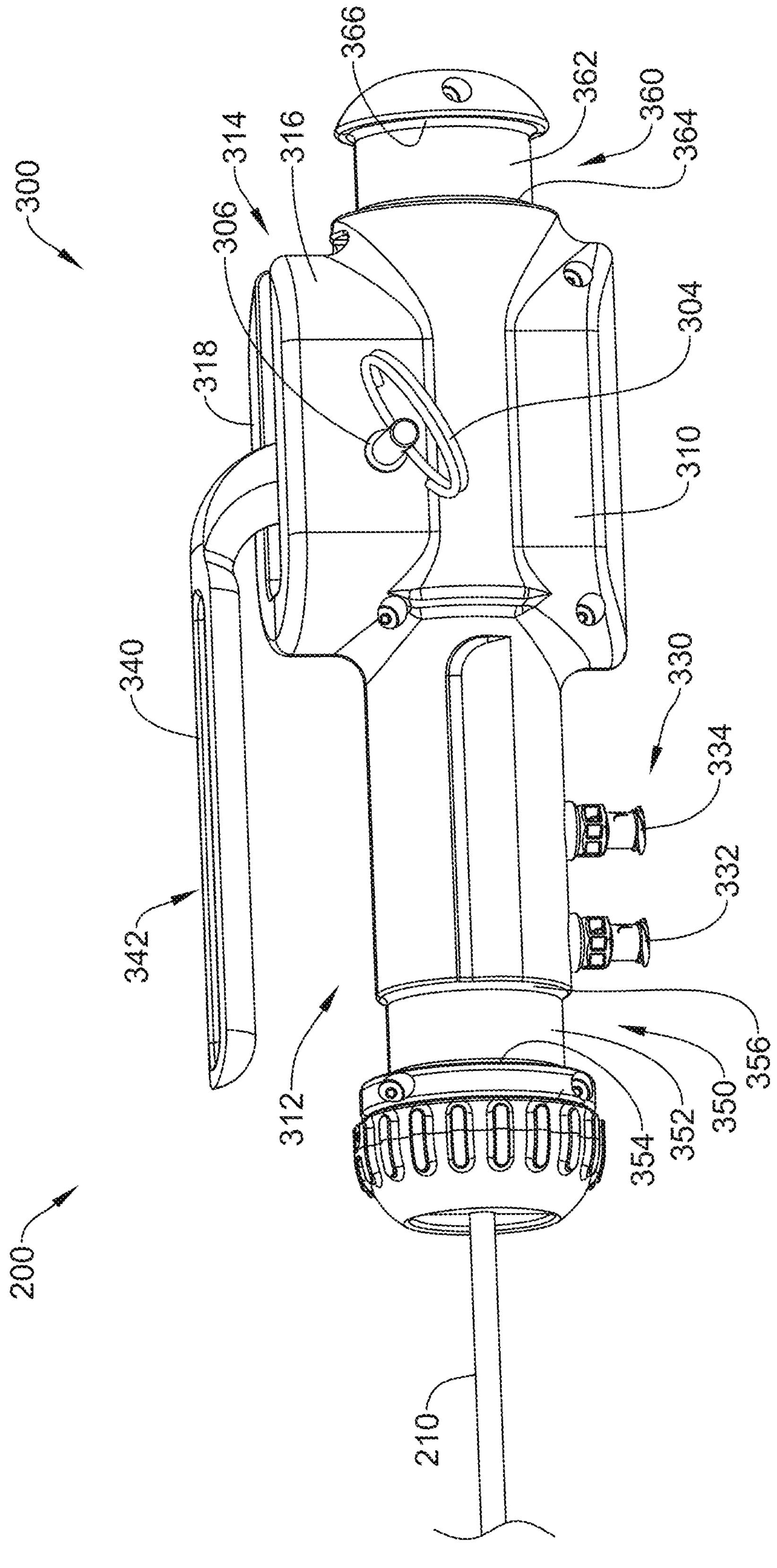

FIG. 2 illustrates selected aspects of the handle 300 and/or the handle housing 310 in greater detail. For clarity, some features and/or elements of the medical device 200 are not shown. In some embodiments, a distal portion 312 of the handle housing 310 may include the one or more ports 330 (e.g., the first port 332, the second port 334, etc.) in fluid communication with the elongate shaft 210. In some embodiments, a proximal portion 314 of the handle housing 310 may include an actuation mechanism configured to translate the cutting blade 260 relative to and/or within the elongate shaft 210. In some embodiments, the actuation mechanism may include a lever arm 340 having a first portion 342 disposed outside of the handle housing 310 and extending distally from the proximal portion 314 of the handle housing 310. In some embodiments, the handle housing 310 may include a left handle housing 316 and a right handle housing 318. In at least some embodiments, the left handle housing 316 and the right handle housing 318 may be assembled together to form the handle housing 310. In some embodiments, the left handle housing 316 and the right handle housing 318 may be assembled together to form the handle housing 310 using removable fasteners (e.g., screws, bolts, etc.), snap fit features, mechanical latches, etc. Other configurations are also contemplated.

The handle housing 310 may include a longitudinally oriented opening extending through a side wall of the handle housing 310. The lever arm 340 may extend through and/or may be movable within the longitudinally oriented opening of the handle housing 310. The lever arm 340 may be movable between an initial position and an actuated position.

In at least some embodiments, the first portion 342 of the lever arm 340 may be oriented parallel to the central longitudinal axis of the elongate shaft 210 in the initial position. In some embodiments, the medical device 200 may include a locking element configured to prevent movement of the lever arm 340 relative to the handle housing 310 and/or within the longitudinally oriented opening. In some embodiments, the locking element may be configured to prevent unintended movement and/or actuation of the lever arm 340. In some embodiments, the locking element may be configured to prevent premature movement and/or actuation of the lever arm 340.

In at least some embodiments, the locking element may include a locking pin 304 configured to engage the handle housing 310 and the lever arm 340 to prevent relative movement therebetween. In some embodiments, the locking pin 304 may be disposed within and/or through the aperture 306 of the handle housing 310 and may engage with the lever arm 340 inside of the handle housing 310 when the lever arm 340 is disposed in the initial position to prevent movement of the lever arm 340 relative to the handle housing 310 (e.g., toward the activated position).

In some embodiments, the locking element may include a ratchet mechanism. In some embodiments, the locking element may include a cam mechanism. In some embodiments, the locking element may include a sliding mechanism and/or a slide lock. In some embodiments, the locking element may include an actuator. In some embodiments, the locking element may include a solenoid. In some embodiments, the locking element may include a knob or a lever. In some embodiments, the locking element may include a frangible connection between lever arm 340 and the handle housing 310. Other configurations are also contemplated.

In some embodiments, the handle 300 may include a grip fixedly attached to the handle housing 310. In some embodiments, the handle housing 310 may include the grip monolithically and/or integrally formed therein. The grip may be configured to be grasped by a hand of a user. In some embodiments, the distal portion 312 of the handle housing 310 may include the grip, may be formed as the grip, and/or may include the grip monolithically and/or integrally formed therein. Other configurations are also contemplated. In some embodiments, the handle housing 310 may be configured to engage and/or be received by a stand 600 (e.g., FIGS. 12-13) as described herein.

In some embodiments, the handle housing 310 may include a first groove 350 configured to engage and/or be received by the stand 600 as described herein. In some embodiments, the first groove 350 may be disposed within the distal portion 312 of the handle housing 310 and/or proximate a distal end of the handle housing 310. Other configurations are also contemplated. In some embodiments, the first groove 350 may include a first circumferential surface 352 extending circumferentially about the handle housing 310 and facing outward from the handle housing 310. The first circumferential surface 352 may be bounded proximally by a first ridge 354 extending circumferentially about the handle housing 310 and the first circumferential surface 352 may be bounded distally by a second ridge 356 extending circumferentially about the handle housing 310.

In some embodiments, the handle housing 310 may include a second groove 360 configured to engage and/or be received by the stand 600 as described herein. In some embodiments, the second groove 360 may be disposed within the proximal portion 314 of the handle housing 310 and/or proximate a proximal end of the handle housing 310. Other configurations are also contemplated. In some embodiments, the second groove 360 may include a second circumferential surface 362 extending circumferentially about the handle housing 310 and facing outward from the handle housing 310. The second circumferential surface 362 may be bounded proximally by a first ridge 364 extending circumferentially about the handle housing 310 and the second circumferential surface 362 may be bounded distally by a second ridge 366 extending circumferentially about the handle housing 310.

Figure 3:
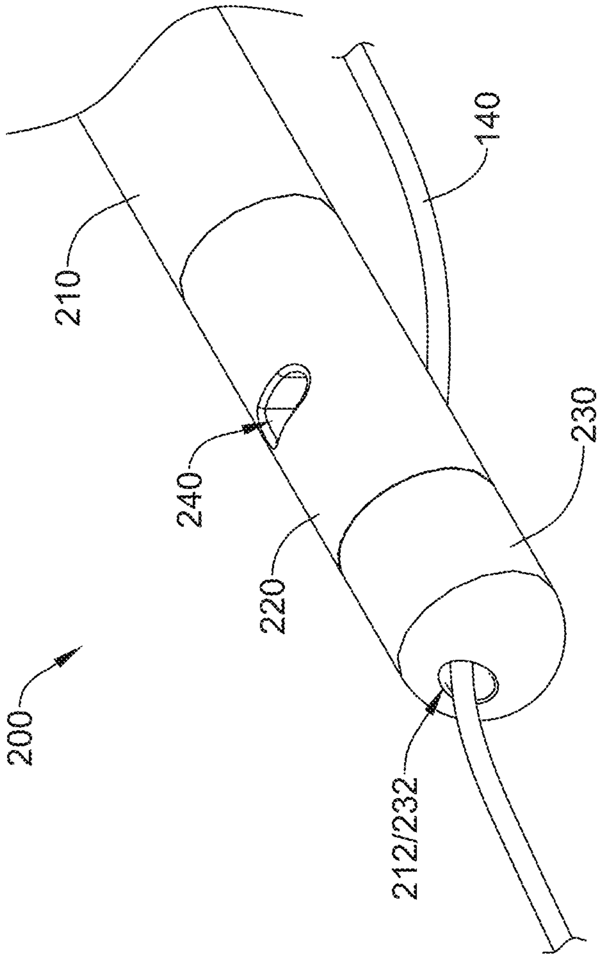

Turning now to FIG. 3, in some embodiments, the elongate shaft 210 and/or the distal tip member 220 may include a distal port 212 configured to receive the suture 140 therein. In some embodiments, the elongate shaft 210 and/or the distal tip member 220 may include a rounded distal cap 230 secured to the distal end of the elongate shaft 210 and/or the distal tip member 220. In some embodiments, the rounded distal cap 230 includes a distal port 232. In some embodiments, the distal port 212 and the distal port 232 may be the same port. In some embodiments, the distal port 212 and the distal port 232 may be in fluid communication with each other. Other configurations are also contemplated. Some suitable but non-limiting materials for the rounded distal cap 230, for example metallic materials, polymer materials, ceramic materials, composite materials, etc., are described below.

The rounded distal cap 230 may be adapted, configured, and/or constructed to substantially avoid and/or prevent entanglement with the plurality of chordae tendineae that may be intact and/or non-ruptured when working within the left ventricle of the heart. In at least some embodiments, the distal port 212 and/or the distal port 232 may be laterally and/or radially offset from the central longitudinal axis of the elongate shaft 210 to facilitate axial translation of the cutting blade 260, as described herein.

In some embodiments, the elongate shaft 210 and/or the distal tip member 220 includes a transverse slot 240 extending radially inward from an outer surface of the elongate shaft 210 and/or an outer surface of the distal tip member 220 generally perpendicular to the central longitudinal axis of the elongate shaft 210. Additional details related to the transverse slot 240 are provided below.

Figure 4:
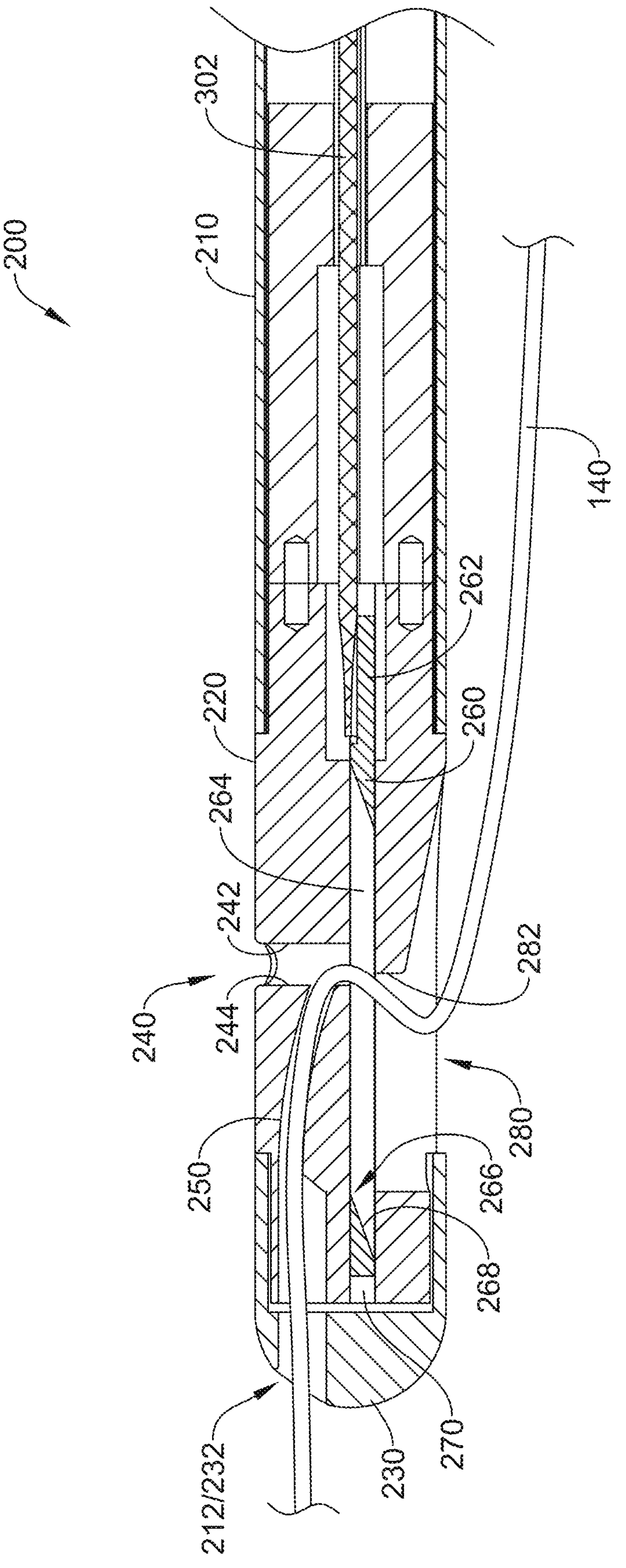
FIG. 4 is a partial cross-sectional view illustrating selected aspects of the medical device of FIGS. 1-3.

FIG. 4 is a partial cross-sectional view illustrating selected elements related to the construction of the medical device 200, the elongate shaft 210, and/or the distal tip member 220 and selected aspects related to cutting the suture 140. In particular, FIG. 4 illustrates elements disposed proximate the distal end of the elongate shaft 210.

In some embodiments, the elongate shaft 210 and/or the distal tip member 220 may include a suture lumen 250 extending proximally within the elongate shaft 210 and/or the distal tip member 220. In some embodiments, the suture lumen 250 may extend from the distal port 212 and/or the distal port 232 axially and/or proximally within the elongate shaft 210, the distal tip member 220, and/or the rounded distal cap 230. In some embodiments, the suture lumen 250 may extend from the distal port 212 and/or the distal port 232 axially and/or proximally within the elongate shaft 210, the distal tip member 220, and/or the rounded distal cap 230 to the transverse slot 240.

In some embodiments, the transverse slot 240 may include and/or may be at least partially defined by a first proximal wall 242 facing distally toward the distal end of the elongate shaft 210 and/or the distal tip member 220. The transverse slot 240 may include and/or may be at least partially defined by a first distal wall 244 facing proximally toward the proximal end of the elongate shaft 210 and/or the distal tip member 220. In some embodiments, the suture lumen 250 may open into the transverse slot 240 through the first distal wall 244.

Figure 4A:
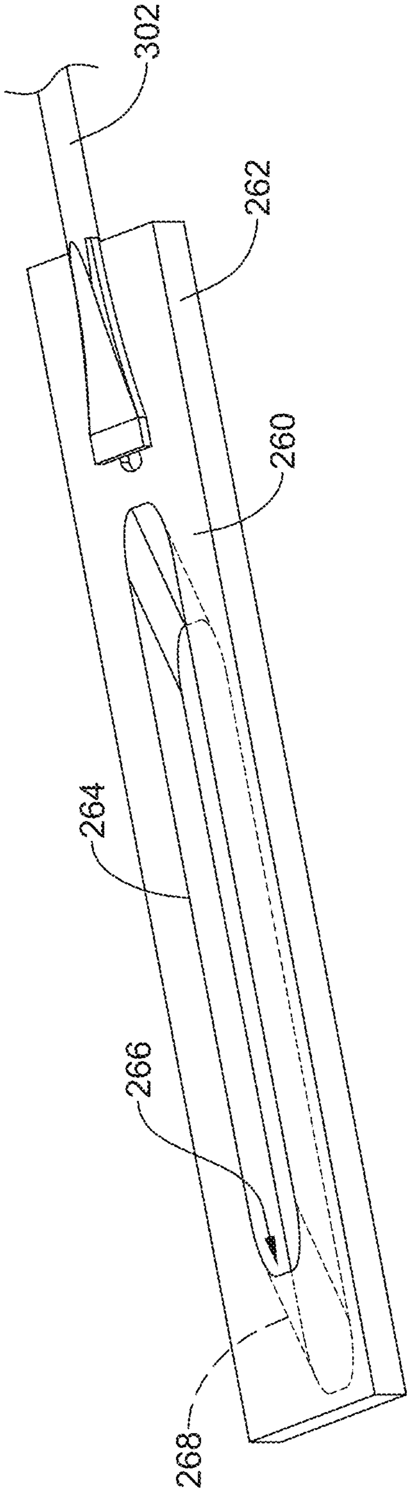
FIG. 4A is a perspective view detailing selected aspects of a cutting blade associated with the medical device.

In some embodiments, the medical device 200 may include a cutting blade 260 disposed proximate the distal end of the elongate shaft 210. A perspective view illustrating selected aspects of the cutting blade 260 in more detail is shown in FIG. 4A for reference. In some embodiments, the cutting blade 260 may include a flattened main body portion 262 oriented substantially parallel to the central longitudinal axis of the elongate shaft 210. The flattened main body portion 262 of the cutting blade 260 may extend from a proximal end of the cutting blade 260 to a distal end of the cutting blade 260. In some embodiments, the cutting blade 260 may include a longitudinally oriented slot 264 extending transversely therethrough and/or extending transversely through the flattened main body portion 262 of the cutting blade 260. In some embodiments, the cutting blade 260 may include a sharpened cutting edge 266 proximate a distal end of the cutting blade 260. In some embodiments, the sharpened cutting edge 266 may face proximally toward the proximal end of the elongate shaft 210 and/or the distal tip member 220. In some embodiments, the sharpened cutting edge 266 may face distally toward the distal end of the elongate shaft 210 and/or the distal tip member 220. In some embodiments, the cutting blade 260 may include a ramp portion 268 extending from a full thickness of the flattened main body portion 262 toward the sharpened cutting edge 266. The ramp portion 268 may be oriented at an oblique angle to the flattened main body portion 262 and/or the central longitudinal axis of the elongate shaft 210.

In some embodiments, the cutting blade 260 may be slidably disposed within a longitudinally extending rectangular slot 270 formed within an interior of the elongate shaft 210 and/or the distal tip member 220. In some embodiments, the cutting blade 260 may be axially translatable within the elongate shaft 210 and/or the distal tip member 220 in response to operation of the actuation mechanism. In some embodiments, the cutting blade 260 may be axially translatable within the longitudinally extending rectangular slot 270 formed within the interior of the elongate shaft 210 and/or the distal tip member 220. In some embodiments, the cutting blade 260 may be axially translatable between a first position and a second position in response to operation of the actuation mechanism.

In some embodiments, the cutting blade 260 may intersect the transverse slot 240 adjacent the suture lumen 250. The suture 140 may be translatable within the suture lumen 250 and/or relative to the elongate shaft 210 and/or the distal tip member 220 when the cutting blade 260 is disposed in the first position and/or when the lever arm 340 is in the initial position. In some embodiments, the first position of the cutting blade 260 may be a distal position, seen in FIG. 4, and the second position of the cutting blade 260 may be a proximal position, seen in FIG. 10. In at least some embodiments, the cutting blade 260 may be non-rotatably disposed within the elongate shaft 210 and/or the distal tip member 220. Some suitable but non-limiting materials for the cutting blade 260, for example metallic materials, polymer materials, ceramic materials, composite materials, etc., are described below.

Returning briefly to FIG. 4, in some embodiments, the elongate shaft 210 and/or the distal tip member 220 may include a side port 280 positioned generally opposite the transverse slot 240 relative to the cutting blade 260. In some embodiments, the side port 280 includes and/or may be at least partially defined by a second proximal wall 282 facing distally toward the distal end of the elongate shaft 210 and/or the distal tip member 220. In some embodiments, the second proximal wall 282 is axially offset from the first proximal wall 242 along the central longitudinal axis of the elongate shaft 210. In some embodiments, the second proximal wall 282 is offset distally from the first proximal wall 242. In some embodiments, the second proximal wall 282 is disposed distal of the first proximal wall 242. In some embodiments, the second proximal wall 282 is oriented generally parallel to the first proximal wall 242.

In some embodiments, the second proximal wall 282 is spaced apart from the first proximal wall 242. In some embodiments, the cutting blade 260 is disposed between the first proximal wall 242 and the second proximal wall 282. In some embodiments, the second proximal wall 282 is spaced apart from the first proximal wall 242 by the cutting blade 260.

In some embodiments, the medical device 200 and/or the actuation mechanism may include a pull wire 302 extending proximally from the cutting blade 260 within the elongate shaft 210. In some embodiments, the pull wire 302 may be fixedly attached to the cutting blade 260. For example, the pull wire 302 may be welded, brazed, soldered, adhesively bonded, or otherwise permanently and fixedly attached to the cutting blade 260. In at least some embodiments, the pull wire 302 may be formed from a metallic material. Other materials and/or configurations are also contemplated. The pull wire 302 may be substantially inelastic and/or may be adapted, configured, and/or constructed to substantially avoid and/or prevent axial stretch. Some suitable but non-limiting materials for the pull wire 302, for example metallic materials, polymer materials, ceramic materials, composite materials, etc., are described below.

Figure 5:
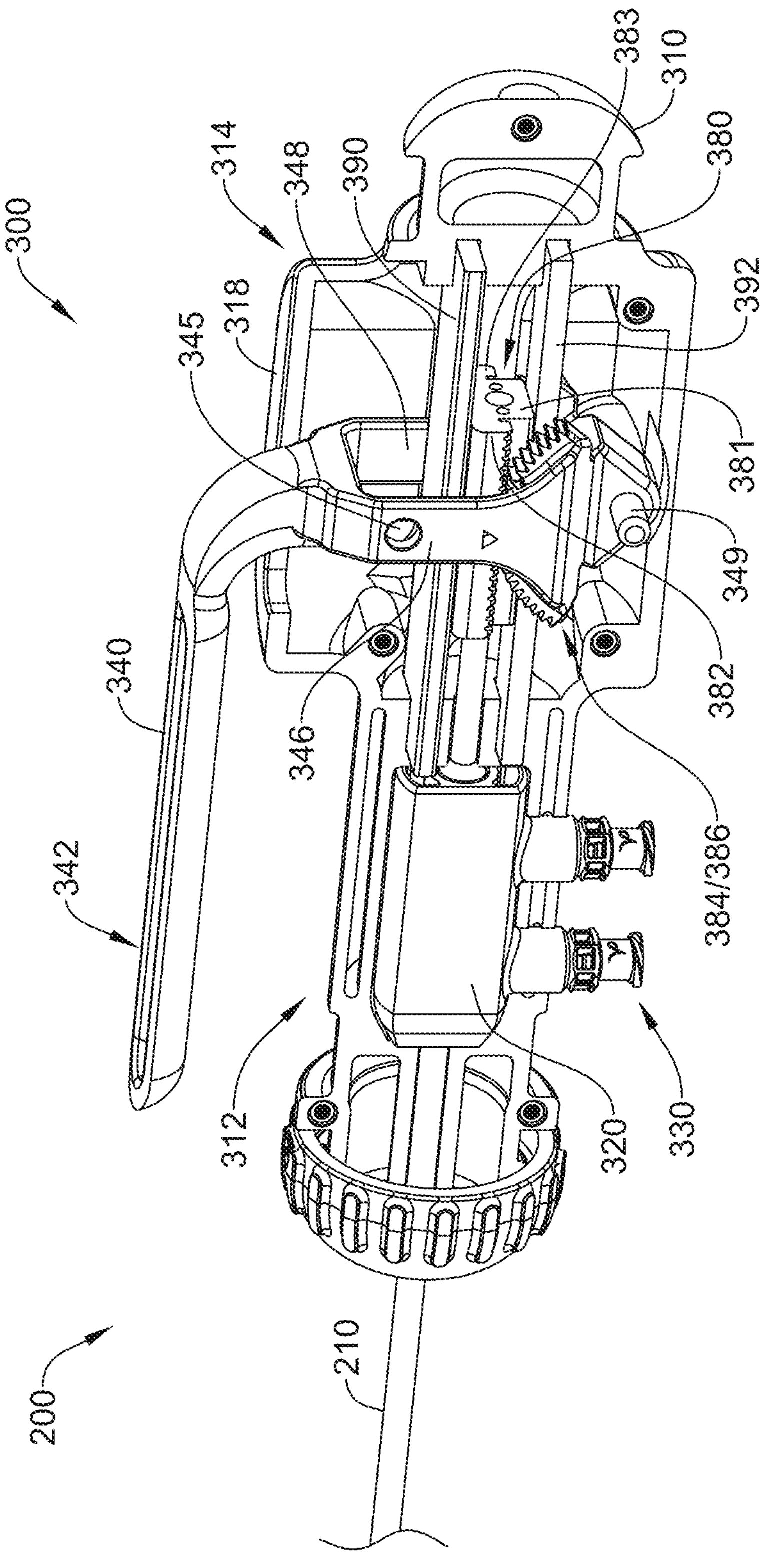
FIGS. 5-7 are partial cutaway views illustrating selected aspects of the medical device of FIGS. 1-3.
Figure 6:
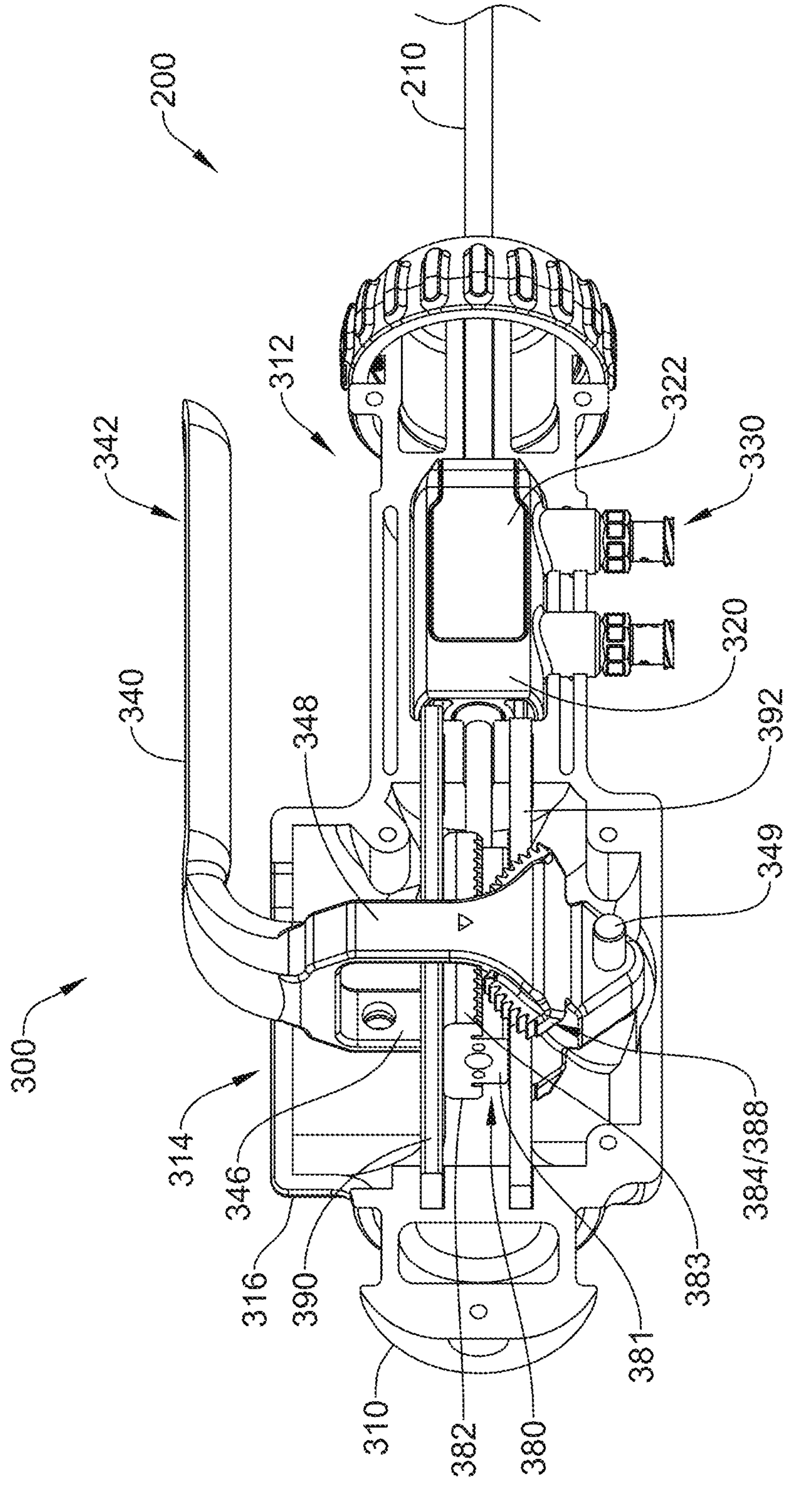
Figure 7:
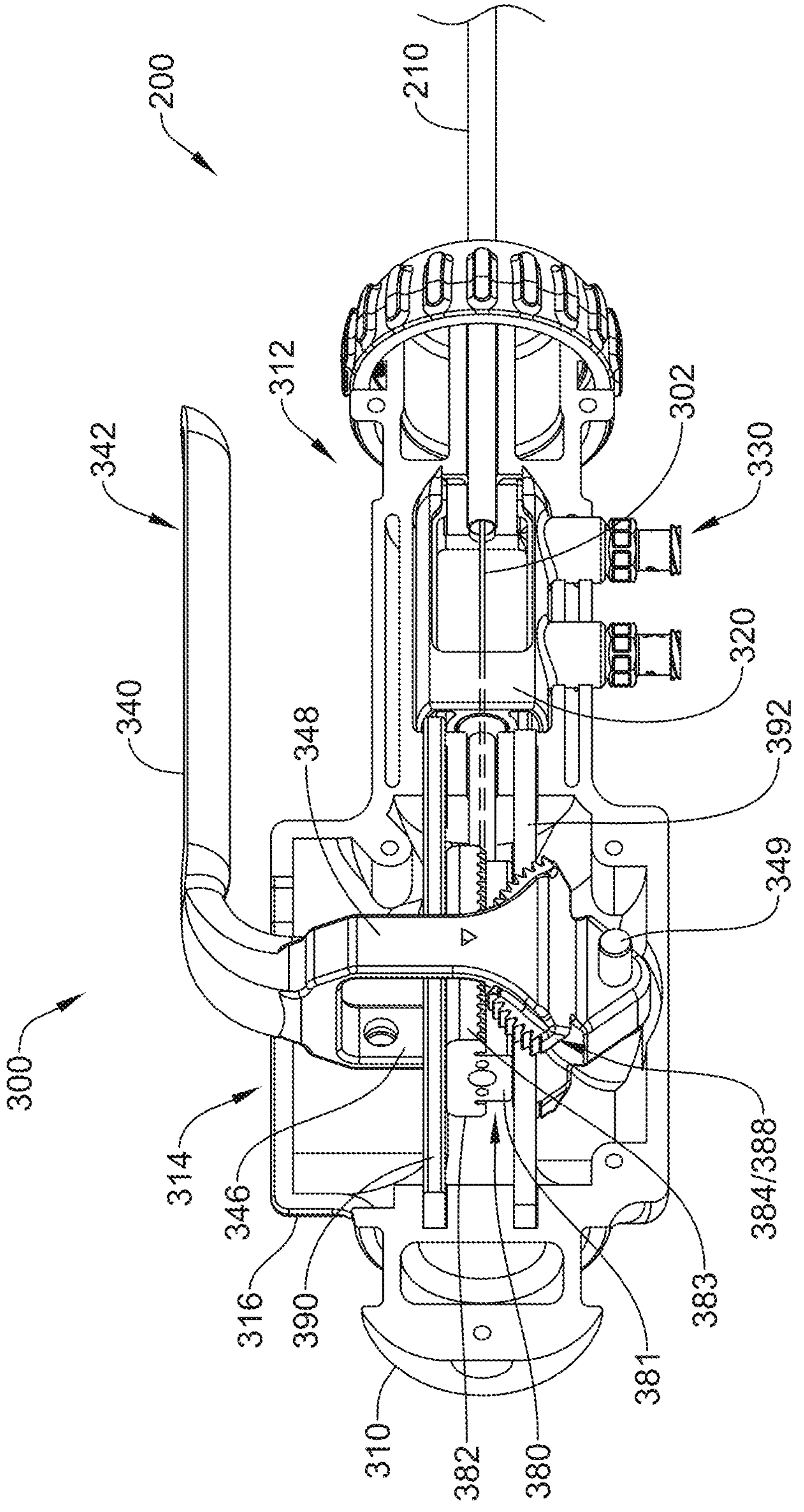

FIGS. 5-7 illustrated selected elements of the medical device 200 and/or the handle 300. In FIG. 5, the left handle housing 316 has been hidden from view and in FIGS. 6-7, the right handle housing 318 has been hidden from view in order to improve understanding. Some elements described herein may be visible in more than one view, and some elements described herein may be visible in one or more views and not visible in one or more other views.

In at least some embodiments, the actuation mechanism may include a rack 380 axially slidable within the handle housing 310. In some embodiments, the rack 380 may be axially slidable parallel to the central longitudinal axis of the elongate shaft 210. In some embodiments, the rack 380 may include a T-shaped cross-section. In some embodiments, the rack 380 may include a central body 381, a first flange 382, and a second flange 383, as seen in FIGS. 5-6. The first flange 382 and the second flange 383 may extend outward from the central body 381 laterally from the central longitudinal axis of the elongate shaft 210.

In some embodiments, the rack 380 may be slidably retained between an upper slide 390 and a lower slide 392. An upper surface of the rack 380 may be oriented parallel with the upper slide 390 and/or the lower slide 392. A lower surface of the rack 380 may be oriented parallel with the upper slide 390 and/or the lower slide 392. In at least some embodiments, the upper slide 390 and/or the lower slide 392 may be oriented parallel to the central longitudinal axis. The upper slide 390 and/or the lower slide 392 may be laterally offset from the central longitudinal axis.

In some embodiments, the first flange 382 may include a first linear gear formed thereon and/or fixedly attached thereto, and the second flange 383 may include a second linear gear formed thereon and/or fixedly attached thereto. In some embodiments, the first linear gear and the second linear gear may be oriented parallel to each other.

In some embodiments, the actuation mechanism may include at least one gear 384 engaged with the rack 380. In some embodiments, the at least one gear 384 may include a semi-circular profile. In at least some embodiments, the at least one gear 384 may be less than circular and/or may extend for less than 360 degrees about an axis of rotation. In some embodiments, the at least one gear 384 may extend for less than 270 degrees about the axis of rotation. In some embodiments, the at least one gear 384 may extend for less than 225 degrees about the axis of rotation. In some embodiments, the at least one gear 384 may extend for less than 180 degrees about the axis of rotation. In some embodiments, the at least one gear 384 may extend for less than 135 degrees about the axis of rotation. In some embodiments, the at least one gear 384 may extend for about 120 degrees, about 105 degrees, about 90 degrees, about 75 degrees, etc. about the axis of rotation.

In some embodiments, the at least one gear 384 may include a first gear 386 configured to engage the rack 380 and a second gear 388 configured to engage the rack 380, as seen in FIGS. 5-6. In some embodiments, the at least one gear 384 may include only one gear (e.g., the first gear 386, the second gear 388, or a different gear). In some embodiments, the at least one gear 384 may include more than two gears. In some embodiments, the first gear 386 may be engaged with the first linear gear and the second gear 388 may be engaged with the second linear gear.

In some embodiments, the at least one gear 384 may be directly engaged with the rack 380. In some embodiments, the first gear 386 may be directly engaged with the first linear gear and the second gear 388 may be directly engaged with the second linear gear. In some embodiments, the at least one gear 384 may be directly engaged with the rack 380 such that a gear ratio of 1:1 is used in the actuation mechanism. While not expressly illustrated, a plurality of gears may be used to form a gear set engaging the rack 380 so as to change the gear ratio to be greater than or less than 1:1. Other configurations are also contemplated. In at least some embodiments, direct engagement between the at least one gear 384 and the rack 380 such that the gear ratio is 1:1 may be preferred.

In some embodiments, a second portion of the lever arm 340 may be disposed inside of the handle housing 310. In some embodiments, the second portion of the lever arm 340 may include a first leg 346 and a second leg 348, as seen in FIGS. 5-6. In at least some embodiments, the first leg 346 may be oriented parallel to the second leg 348. In some embodiments, the first leg 346 and the second leg 348 may be oriented transversely relative to the first portion 342 of the lever arm 340. In some embodiments, the first leg 346 and the second leg 348 may be oriented perpendicular to the first portion 342 of the lever arm 340. In some embodiments, the first leg 346 and the second leg 348 may be oriented transversely relative to the central longitudinal axis of the elongate shaft 210 in the initial position. In some embodiments, the first leg 346 and the second leg 348 may be disposed on opposite sides of the central longitudinal axis of the elongate shaft 210. In some embodiments, the first leg 346 and the second leg 348 may be disposed radially outward from the rack 380 relative to the central longitudinal axis of the elongate shaft 210. In some embodiments, the first leg 346 and the second leg 348 may be disposed on opposite sides of the rack 380.

In some embodiments, the second portion of the lever arm 340 may be coupled to the at least one gear 384. In some embodiments, the first leg 346 and the second leg 348 may be coupled to the at least one gear 384. In some embodiments, the first leg 346 may be coupled to the first gear 386 and the second leg 348 may be coupled to the second gear 388. In some embodiments, the first leg 346 may be fixedly attached to the first gear 386 and the second leg 348 may be fixedly attached to the second gear 388. In some embodiments, the first leg 346 may be monolithically and/or integrally formed with the first gear 386 and the second leg 348 may be monolithically and/or integrally formed with the second gear 388. Other configurations are also contemplated.

In some embodiments, the lever arm 340 and/or the second portion of the lever arm 340 may be pivotably coupled to the handle housing 310. In some embodiments, the lever arm 340 may be configured to pivot and/or rotate about a pivot pin 349. In some embodiments, the pivot pin 349 may be configured to engage with one or more recesses formed in the handle housing 310 (e.g., the left handle housing 316, the right handle housing 318, etc.). In some embodiments, the pivot pin 349 may be monolithically and/or integrally formed with the second portion of the lever arm 340. In some embodiments, the pivot pin 349 may be monolithically and/or integrally formed with the handle housing 310, the left handle housing 316, and/or the right handle housing 318. In some embodiments, the pivot pin 349 may be a separate element from the lever arm 340, the handle housing 310, the left handle housing 316, and/or the right handle housing 318.

In some embodiments, the first leg 346 of the lever arm 340 may include an aperture 345 disposed therein, as seen in FIG. 5. The aperture 345 of the first leg 346 may be aligned with the aperture 306 of the handle housing 310 when the lever arm 340 is in the initial position. In some embodiments, the locking pin 304 (e.g., FIG. 2) may be configured to extend into and/or through the aperture 306 of the handle housing 310 and the aperture 345 of the first leg 346 when the lever arm 340 is in the initial position to prevent movement of the lever arm 340 relative to the handle housing 310 (e.g., toward the activated position). Other locking elements, as discussed herein, are also contemplated.

In some embodiments, the handle housing 310 may include an internal chamber 320 in fluid communication with the one or more ports 330 attached to the handle housing 310, as seen in FIGS. 5-7. The internal chamber 320 may include a chamber cover 322. In some embodiments, the chamber cover 322 may be removable from the internal chamber 320. In some embodiments, the internal chamber 320 may be in fluid communication with the elongate shaft 210 and the one or more ports 330. In some embodiments, the fluid source may supply a fluid such as a saline solution or other biocompatible fluid into the internal chamber 320 and/or the elongate shaft 210 and the vacuum source may suction and/or remove air bubbles, debris, contamination, etc. from the internal chamber 320 and/or the elongate shaft 210. Other configurations are also contemplated. In at least some embodiments, the pull wire 302 may pass through the internal chamber 320, as seen in FIG. 7, which has the chamber cover 322 removed. In some embodiments, the cutting blade 260 may be operably coupled to the rack 380. In some embodiments, the cutting blade 260 may be operably coupled to the rack 380 by the pull wire 302. In some embodiments, the pull wire 302 may extend distally from the rack 380 to the cutting blade 260. In some embodiments, the pull wire 302 may be secured to the rack 380. In some embodiments, the pull wire 302 may be fixedly attached to the rack 380.

Figure 8:
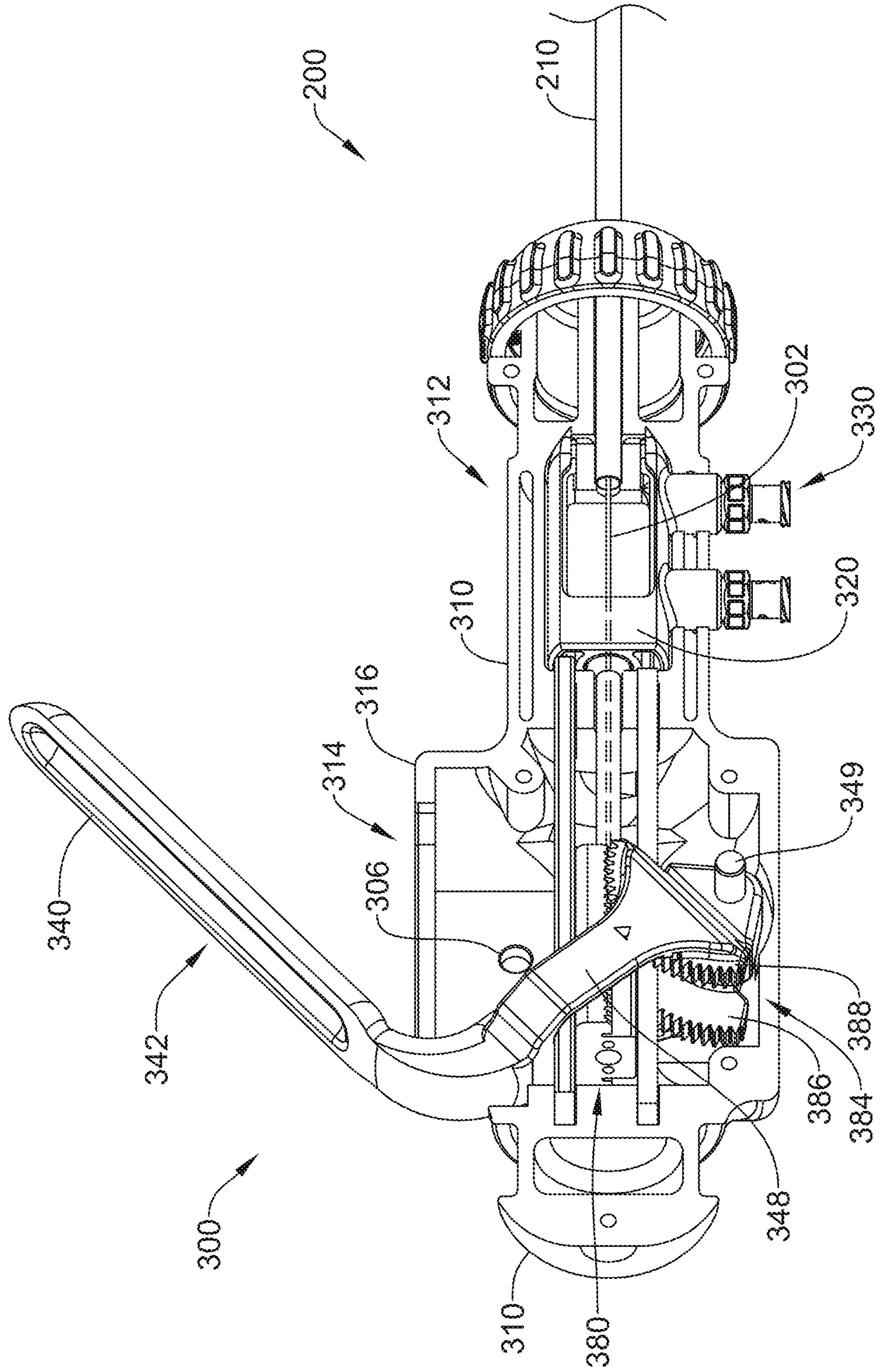
FIGS. 8-11 illustrate selected aspects related to the use of the medical device.
Figure 9:
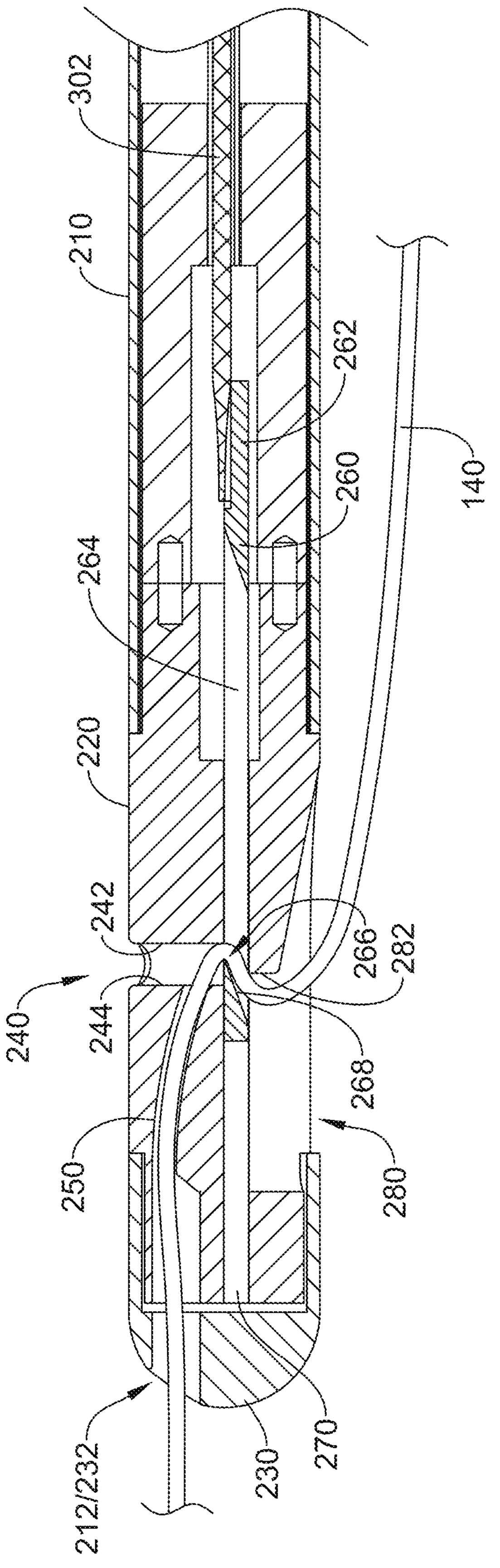
Figure 10:
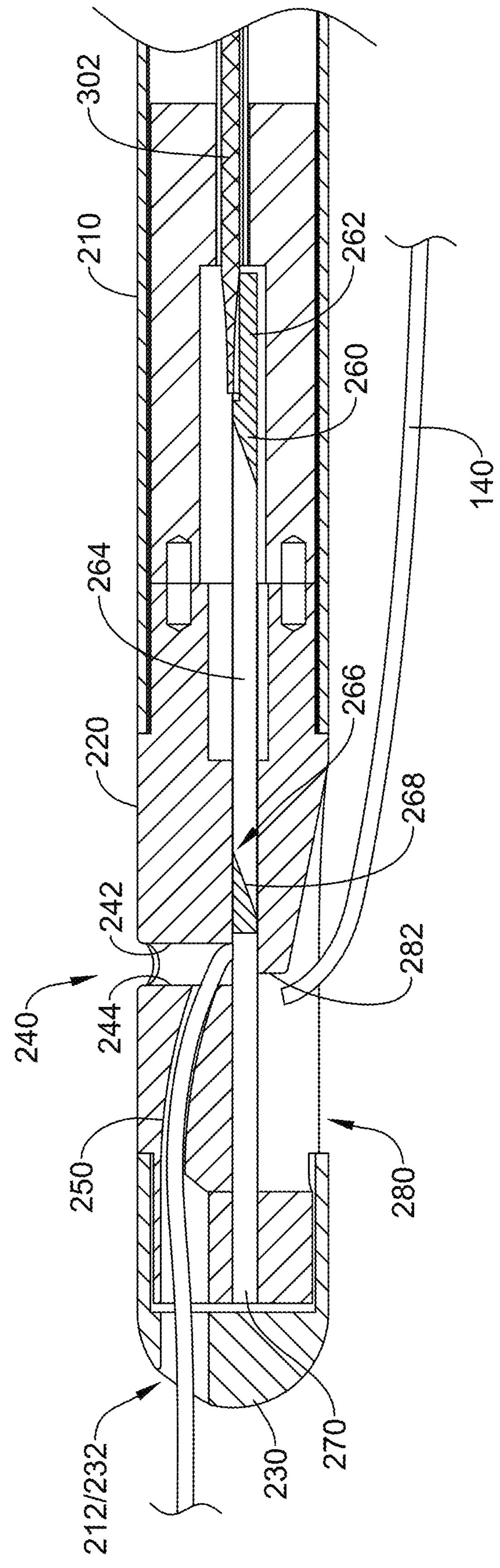

In some embodiments, translation of the first portion of the lever arm 340 relative to the handle housing 310 may axially translate the rack 380 within the handle housing 310, as seen in FIG. 8. In some embodiments, translation of the first portion of the lever arm 340 away from the handle housing 310 may axially translate the rack 380 within the handle housing 310. In some embodiments, translation of the first portion of the lever arm 340 away from the handle housing 310 may axially translate the rack 380 proximally within the handle housing 310. In some embodiments, translation of the first portion of the lever arm 340 relative to the handle housing 310 may axially translate the cutting blade 260 within the elongate shaft 210 and/or the distal tip member 220 to cut the suture 140, as seen in FIGS. 9-10.

In some embodiments, proximal axial translation of the cutting blade 260 relative to the elongate shaft 210 and/or the distal tip member 220 and/or within the longitudinally extending rectangular slot 270 formed within an interior of the elongate shaft 210 and/or the distal tip member 220 (via proximal translation of the pull wire 302, for example) may translate the sharpened cutting edge 266 of the cutting blade 260 toward the transverse slot 240 and/or the first proximal wall 242 that at least partially defines the transverse slot 240.

With respect to operation of the medical device 200 and/or the cutting blade 260, when the suture 140 extends within the suture lumen 250, into the transverse slot 240, through the longitudinally oriented slot 264 formed in the flattened main body portion 262 of the cutting blade 260, and out the side port 280, and the cutting blade 260 is in the first position, as shown in FIG. 4, the suture 140 may be axially translatable within the suture lumen 250, the longitudinally oriented slot 264, and the side port 280. When the suture 140 extends within the suture lumen 250, into the transverse slot 240, through the longitudinally oriented slot 264 formed in the flattened main body portion 262 of the cutting blade 260, and out the side port 280, and the cutting blade 260 is translated toward (e.g., proximally) the second position and/or relative to and/or within the elongate shaft 210 and/or the distal tip member 220, as shown in FIG. 9, the suture 140 may become pinched between the second proximal wall 282 and the ramp portion 268 of the cutting blade 260 such that the suture 140 may bias the sharpened cutting edge 266 of the cutting blade 260 away from the second proximal wall 282 and toward the first proximal wall 242 such that further axial and/or proximal translation of the cutting blade 260 relative to and/or within the elongate shaft 210 and/or the distal tip member 220 causes cooperation between the sharpened cutting edge 266 of the cutting blade 260 and the first proximal wall 242 to cut the suture 140 extending through the longitudinally oriented slot 264 of the cutting blade 260 within the elongate shaft 210 and/or the distal tip member 220, as shown in FIG. 10.

In some embodiments, the medical device 200 may include, and/or the first proximal wall 242 and the second proximal wall 282 may define, a stepped offset through the longitudinally oriented slot 264 of the flattened main body portion 262 of the cutting blade 260. The ramp portion 268 and the second proximal wall 282 may cooperate to use the suture 140 itself to bias the cutting blade 260 toward the first proximal wall 242, which forms and/or acts as a shearing surface. As a result of this configuration, biasing springs and/or super-tight tolerances are not necessary to achieve a clean cut of the suture 140. This may be particularly useful for suture materials that undergo at least some degree of compression before they can be or are cut. For example, some materials may have and/or include a number of air gaps within the material itself which may be compressed and/or squeezed before any cutting occurs. If too much gap or lateral movement between the cutting blade and the shearing surface (e.g., the first proximal wall) is present in the device, the suture may be squeezed and/or pinched between the surfaces without properly cutting, which could lead to stretching, thinning without cutting, tearing, material shaving or scraping, binding, excessive force requirements for axial translation of the cutting blade, etc.

Figure 11:
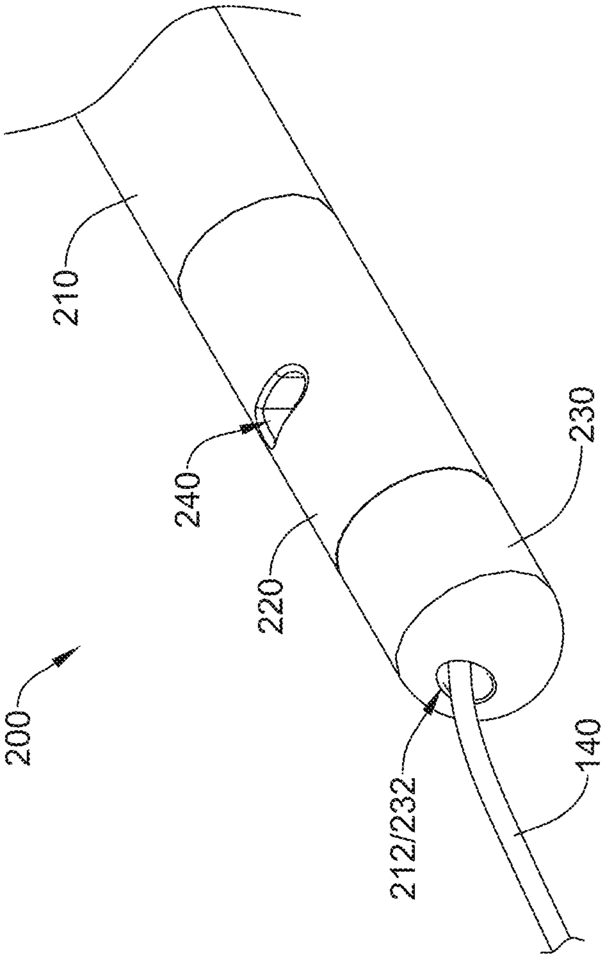

For reference, FIG. 11 illustrates a perspective view of the distal tip member 220 of the medical device 200 of FIG. 10 after severing the suture 140 and a proximal portion of the suture 140 has been removed.

Figure 12:
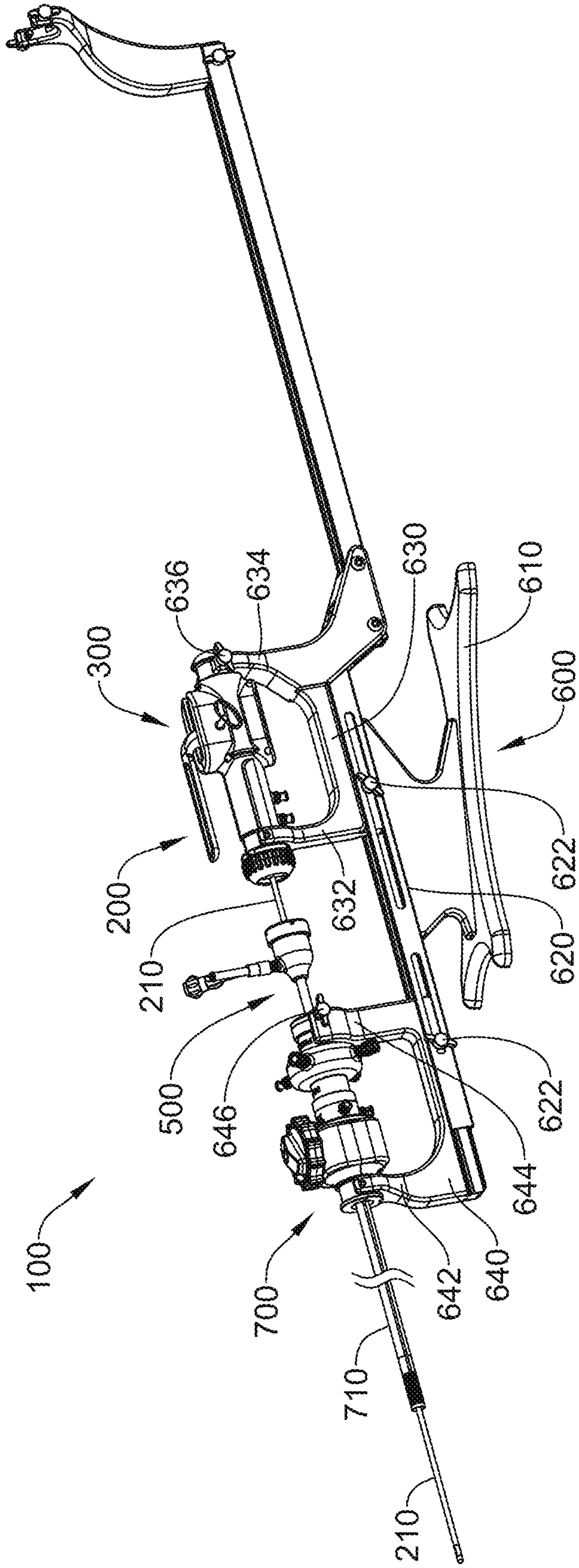
FIG. 12 illustrates selected aspects of a medical device system associated with the disclosure.
Figure 13:
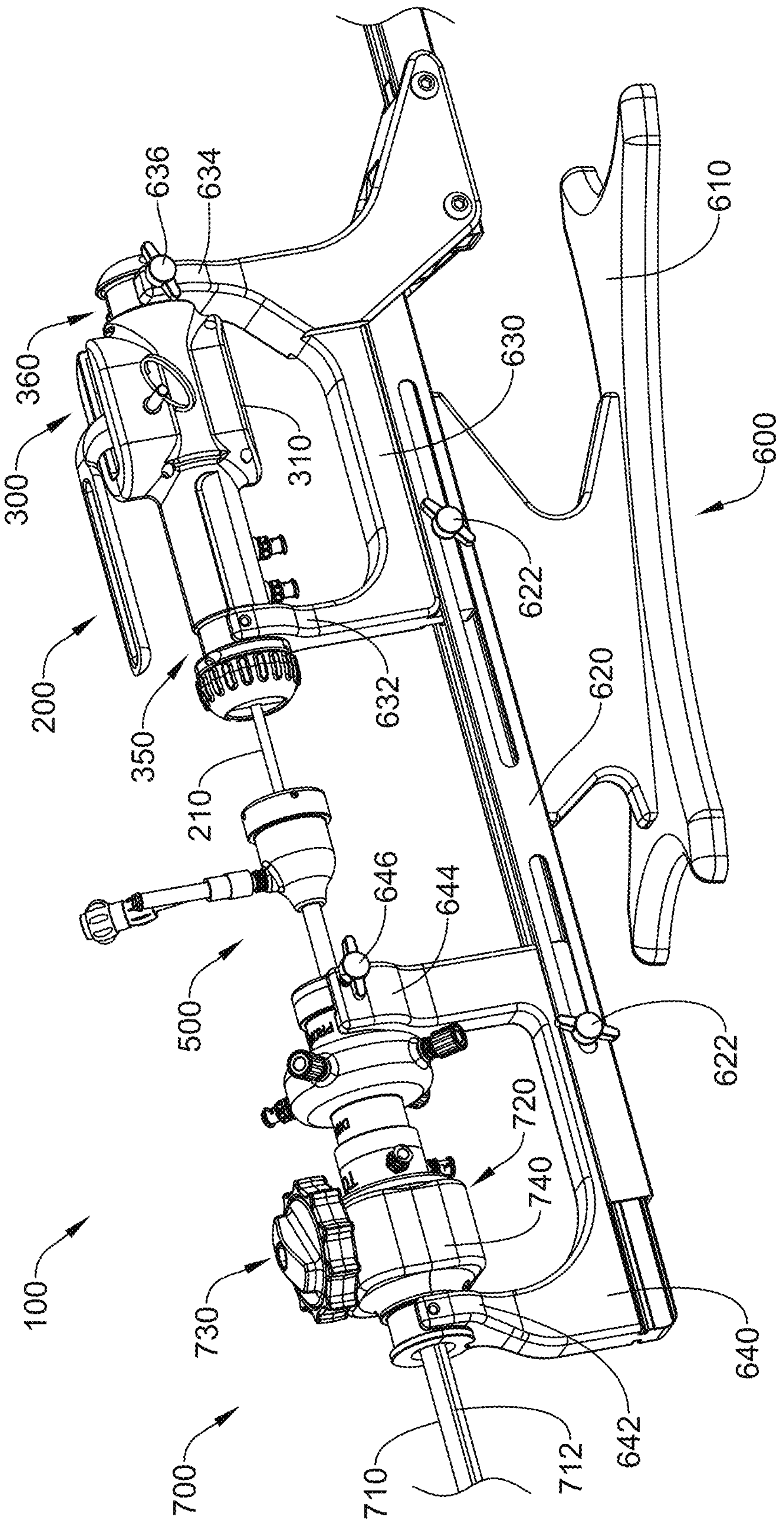
FIG. 13 illustrates selected aspects of the medical device system of FIG. 12 is greater detail.

FIGS. 12-13 illustrate selected aspects of a medical device system 100. The medical device system 100 may include a stand 600 configured to support at least one medical device. In some embodiments, the medical device system 100 may include the medical device 200. The medical device 200 may be couplable and/or securable to the stand 600.

In some embodiments, the stand 600 may include a base 610. In some embodiments, the base 610 may be configured to be secured to a table. In some embodiments, the base 610 may be configured to be secured to a surgical robot. Other configurations are also contemplated. In some embodiments, the stand 600 may include a slide rail 620 coupled thereto. In some embodiments, the slide rail 620 may be fixedly attached to the base 610.

In some embodiments, the stand 600 may include a support member 630 slidably coupled to the slide rail 620. In some embodiments, at least one fastening element 622 (e.g., a set screw, a thumb screw, a friction lock, etc.) may be configured to secure the support member 630 to and/or relative to the slide rail 620. In some embodiments, the support member 630 may include a first yoke 632 configured to engage the handle housing 310 of the medical device 200 and a second yoke 634 configured to engage the handle housing 310 of the medical device 200. In some embodiments, the first groove 350 and/or the first circumferential surface 352 may be configured to engage the first yoke 632 and the second groove 360 and/or the second circumferential surface 362 may be configured to engage the second yoke 634. In some embodiments, the first yoke 632 may include a generally U-shaped portion and may be configured to receive the first groove 350 and/or the first circumferential surface 352 within the generally U-shaped portion thereof. In some embodiments, the second yoke 634 may include a generally U-shaped portion and may be configured to receive the second groove 360 and/or the second circumferential surface 362 within the generally U-shaped portion thereof. In some embodiments, the support member 630 may include at least one fastening element 636 (e.g., a set screw, a thumb screw, a friction lock, etc.) configured to secure the medical device 200 and/or the handle housing 310 to and/or relative to the support member 630.

In some embodiments, the stand 600 may include a second support member 640 slidably coupled to the slide rail 620. In some embodiments, at least one fastening element 622 (e.g., a set screw, a thumb screw, a friction lock, etc.) may be configured to secure the second support member 640 to and/or relative to the slide rail 620. In some embodiments, the second support member 640 may include a first yoke 642 configured to engage a second medical device (e.g., the steering system 700, discussed further below) and a second yoke 644 configured to engage the second medical device in a manner similar to the first yoke 632 and the second yoke 634 engaging the medical device 200 and/or the handle housing 310 above. In some embodiments, the first yoke 642 may include a generally U-shaped portion and may be configured to receive the second medical device within the generally U-shaped portion thereof. In some embodiments, the second yoke 644 may include a generally U-shaped portion and may be configured to receive the second medical device within the generally U-shaped portion thereof. In some embodiments, the second support member 640 may include at least one fastening element 646 (e.g., a set screw, a thumb screw, a friction lock, etc.) configured to secure the second medical device to and/or relative to the second support member 640.

In some embodiments, the medical device system 100 may include the second medical device couplable and/or securable to the stand 600 and/or the second support member 640. In some embodiments, the second medical device may include a steering system 700 for a steerable flexible elongate member 710. In some embodiments, the steering system 700 may include a handle 720. The steerable flexible elongate member 710 may extend distally from the handle 720. In some embodiments, the handle 720 may include a control knob 730 mounted on a housing block 740. The handle 720 and/or the housing block 740 may be engageable with and/or couplable to the second support member 640. In some embodiments, at least some working components of the handle 720 and/or the steering system 700 may be disposed within and/or supported by the housing block 740. In one example, the steering system 700 may include a gear system disposed within the housing block 740 and operatively coupled to and/or associated with the control knob 730. Other configurations are also contemplated.

In some embodiments, the steering system 700 may include one or more flexible elongate steering elements 712 extending along and/or within the steerable flexible elongate member 710 from the housing block 740. In some embodiments, the gear system may be operatively engaged with and/or associated with the one or more flexible elongate steering elements 712. In one example, the gear system may be configured to apply tension to the one or more flexible elongate steering elements 712 to selectively deflect, bend, and/or steer a distal portion and/or a distal tip of the steerable flexible elongate member 710. In some embodiments, the steering system 700 may be configured to deflect, bend, and/or steer the distal portion and/or the distal tip of the steerable flexible elongate member 710 in at least one direction within a plane of deflection. In some embodiments, the steering system 700 may be configured to deflect, bend, and/or steer the distal portion and/or the distal tip of the steerable flexible elongate member 710 in two opposing directions within the plane of deflection. Other configurations are also contemplated.

In some embodiments, the steerable flexible elongate member 710 may extend away from the second support member 640. The steering system 700 may be configured to receive the elongate shaft 210 of the medical device 200 within the steerable flexible elongate member 710, as seen in FIG. 12. In at least some embodiments, the steering system 700 may be configured to slidably receive the elongate shaft 210 of the medical device 200 within the steerable flexible elongate member 710. In some embodiments, the stand 600 may be used to axially fix the elongate shaft 210 relative to the steerable flexible elongate member 710. Other configurations are also contemplated.

In some embodiments, the medical device system 100 may optionally include an adapter device 500. In some embodiments, the adapter device 500 may be configured to receive the elongate shaft 210 of the medical device 200 at a proximal end and may extend into the steering system 700 and/or the steerable flexible elongate member 710 at a distal end. In some embodiments, the steerable flexible elongate member 710 may have an inner diameter that is greater than an outer diameter of the elongate shaft 210. In some embodiments, the steerable flexible elongate member 710 may be configured to receive more than one type of medical device and/or more than one size of medical device. In some embodiments, the adapter device 500 may provide a size adjustment between the elongate shaft 210 and the steerable flexible elongate member 710 to prevent fluid leaks, while permitting the steerable flexible elongate member 710 to receive medical devices having an outer diameter larger than the outer diameter of the elongate shaft 210.

In some embodiments, the support member 630 may be configured to receive and/or support one or more additional medical devices. In some embodiments, the one or more additional medical devices may be interchangeably received and/or engaged by the first yoke 632 and/or the second yoke 634 of the support member 630.

Figure 14:
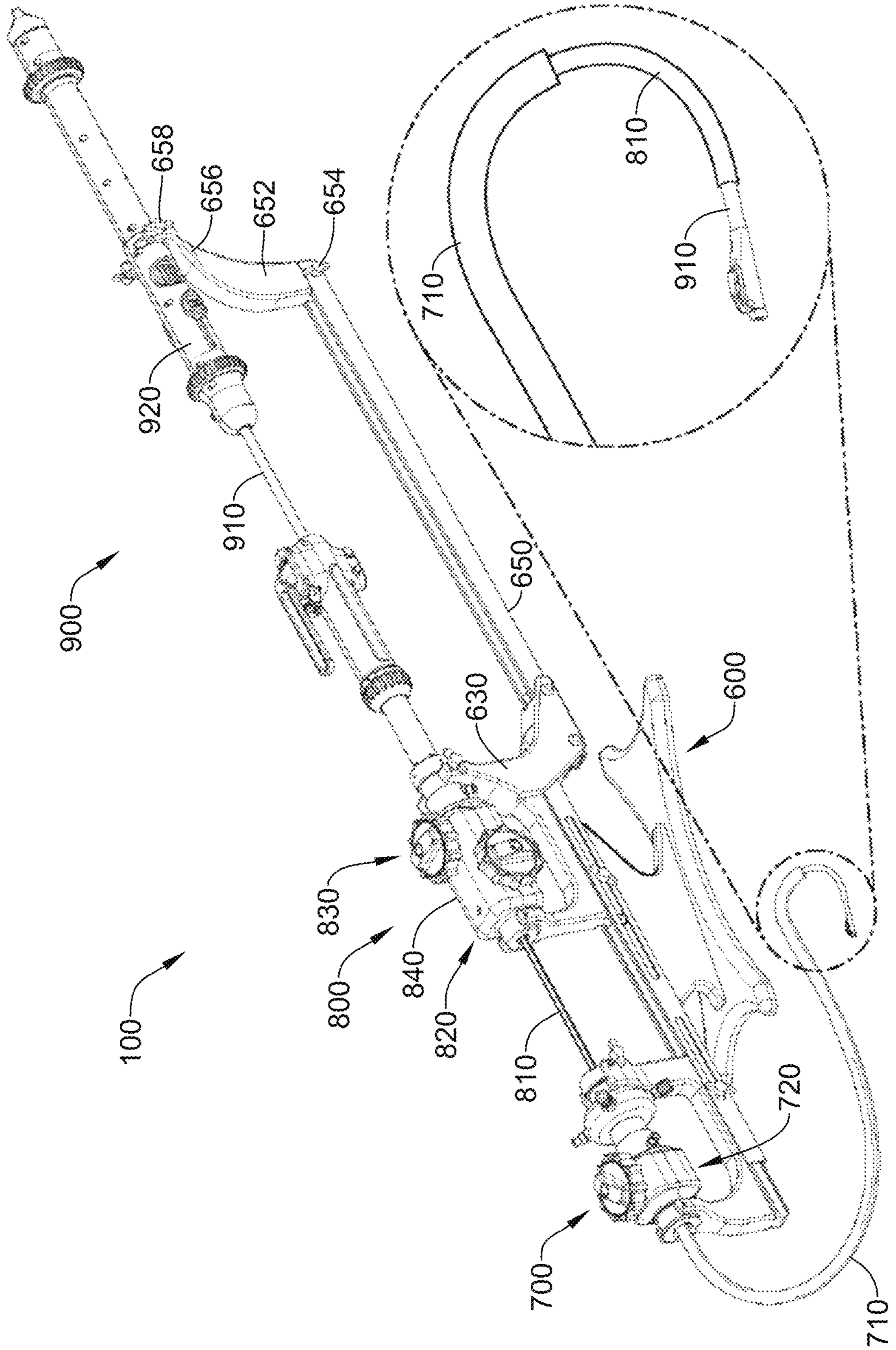
FIG. 14 illustrates selected aspects of an alternative configuration of the medical device system.

In one example, illustrated in FIG. 14, the one or more additional medical devices may include a second steering system 800 for a second steerable flexible elongate member 810. In some embodiments, the second steering system 800 may include a handle 820. The second steerable flexible elongate member 810 may extend distally from the handle 820. In some embodiments, the handle 820 may include one or more control knobs 830 mounted on a housing block 840. The handle 820 and/or the housing block 840 may be engageable with and/or couplable to the support member 630. In some embodiments, at least some working components of the handle 820 and/or the second steering system 800 may be disposed within and/or supported by the housing block 840. In one example, the second steering system 800 may include a gear system disposed within the housing block 840 and operatively coupled to and/or associated with the one or more control knobs 830. Other configurations are also contemplated.

In some embodiments, the second steering system 800 may include one or more flexible elongate steering elements extending along and/or within the second steerable flexible elongate member 810 from the housing block 840. In some embodiments, the gear system may be operatively engaged with and/or associated with the one or more flexible elongate steering elements. In one example, the gear system may be configured to apply tension to the one or more flexible elongate steering elements to selectively deflect, bend, and/or steer a distal portion and/or a distal tip of the second steerable flexible elongate member 810. In some embodiments, the second steering system 800 may be configured to deflect, bend, and/or steer the distal portion and/or the distal tip of the second steerable flexible elongate member 810 in at least one direction within a plane of deflection. In some embodiments, the second steering system 800 may be configured to deflect, bend, and/or steer the distal portion and/or the distal tip of the second steerable flexible elongate member 810 in two opposing directions within the plane of deflection.

In some embodiments, the second steering system 800 may be configured to deflect, bend, and/or steer the distal portion and/or the distal tip of the second steerable flexible elongate member 810 in at least one direction within two different planes of deflection. As such, in at least some embodiments, the second steering system 800 may be configured to provide four-way steering. In some embodiments, the second steering system 800 may be configured to deflect, bend, and/or steer the distal portion and/or the distal tip of the second steerable flexible elongate member 810 in two opposing directions within each of the two different planes of deflection. In some embodiments, the two different planes of deflection may be oriented perpendicular to each other. Other configurations are also contemplated.

In some embodiments, the second steerable flexible elongate member 810 may extend away from the support member 630 and/or may extend into the steerable flexible elongate member 710 of the steering system 700. The second steering system 800 may be configured to receive an elongate shaft 910 of a third medical device 900 within the second steerable flexible elongate member 810, as seen in FIG. 14. In at least some embodiments, the second steering system 800 may be configured to slidably receive the elongate shaft 910 of the third medical device 900 within the second steerable flexible elongate member 810. Other configurations are also contemplated In some embodiments, the stand 600 may include an extension arm 650 extending proximally from the support member 630. In some embodiments, the extension arm 650 may be fixedly attached to the support member 630. In some embodiments, the extension arm 650 may include a third support member 652 slidably coupled to the extension arm 650. In some embodiments, at least one fastening element 654 (e.g., a set screw, a thumb screw, a friction lock, etc.) may be configured to secure the third support member 652 to and/or relative to the extension arm 650. In some embodiments, the third support member 652 may include a yoke 656 configured to engage the third medical device 900, as seen in FIG. 14, in a manner similar to the first yoke 632 and the second yoke 634 engaging the medical device 200 and/or the handle housing 310 above. In some embodiments, the yoke 656 may include a generally U-shaped portion and may be configured to receive the third medical device 900 within the generally U-shaped portion thereof. In some embodiments, the third support member 652 may include at least one fastening element 658 (e.g., a set screw, a thumb screw, a friction lock, etc.) configured to secure the third medical device 900 to and/or relative to the third support member 652.

In some embodiments, the third medical device 900 may include a delivery and deployment system configured to deliver, operate, and/or deploy an implantable device. In some embodiments, the third medical device 900 may include a handle 920 configured to engage the third support member 652 and/or the yoke 656 of the third support member 652.

The materials that can be used for the various components of the medical device and the various elements thereof disclosed herein may include those commonly associated with medical devices. For simplicity purposes, the following discussion refers to the system. However, this is not intended to limit the devices and methods described herein, as the discussion may be applied to other elements, members, components, or devices disclosed herein, such as, but not limited to, the medical device, the medical device system, the elongate shaft, the handle housing, the cutting blade, the pull wire, the lever arm, etc. and/or elements or components thereof.

In some embodiments, the system and/or components thereof may be made from a metal, a metal alloy, a polymer, a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN®), polyether block ester, polyurethane, polypropylene (PP), polyvinylchloride (PVC), polyether-ester (for example, ARNITEL®), ether or ester based copolymers (for example, butylene/poly(alkylene ether) phthalate and/or other polyester elastomers such as HYTREL®), polyamide (for example, DURETHAN® or CRISTAMID®), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID®), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, polyurethane silicone copolymers (for example, Elast-Eon® or ChronoSil®), biocompatible polymers, other suitable materials, or mixtures, combinations, copolymers thereof, polymer/metal composites, and the like. In some embodiments, the system and/or components thereof can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; platinum; palladium; gold; combinations thereof; or any other suitable material.

In at least some embodiments, portions or all of the system and/or components thereof may also be doped with, made of, or otherwise include a radiopaque material. Radiopaque materials are understood to be materials capable of producing a relatively bright image on a fluoroscopy screen or another imaging technique (e.g., ultrasound, etc.) during a medical procedure. This relatively bright image aids the user of the system in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the system to achieve the same result.

In some embodiments, a degree of Magnetic Resonance Imaging (MRI) compatibility is imparted into the system and/or other elements disclosed herein. For example, the system and/or components or portions thereof may be made of a material that does not substantially distort the image and create substantial artifacts (e.g., gaps in the image). Certain ferromagnetic materials, for example, may not be suitable because they may create artifacts in an MRI image. The system or portions thereof may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, the system and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethyl ketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl ketone, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); immunosuppressants (such as the "olimus" family of drugs, rapamycin analogues, macrolide antibiotics, biolimus, everolimus, zotarolimus, temsirolimus, picrolimus, novolimus, myolimus, tacrolimus, sirolimus, pimecrolimus, etc.); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The scope of the disclosure is, of course, defined in the language in which the appended claims are expressed.

What is claimed is:

1. A medical device for cutting a suture during a minimally invasive procedure, comprising:
- an elongate shaft having a proximal end, a distal end, and a central longitudinal axis extending from the proximal end to the distal end;
- a handle housing disposed at the proximal end of the elongate shaft; and
- a cutting blade disposed proximate the distal end of the elongate shaft;
- wherein a proximal portion of the handle housing includes an actuation mechanism including a lever arm having a first portion disposed outside of the handle housing and extending distally from the proximal portion of the handle housing; wherein the actuation mechanism includes a rack axially slidable parallel to the central longitudinal axis and at least one gear engaged with the rack; wherein the at least one gear includes a semi-circular profile;
- wherein translation of the first portion of the lever arm relative to the handle housing axially translates the cutting blade within the elongate shaft.

2. The medical device of claim 1, wherein a second portion of the lever arm disposed inside of the handle housing is coupled to the at least one gear.

3. The medical device of claim 1, wherein the cutting blade is operably coupled to the rack.

4. The medical device of claim 1, wherein translation of the first portion of the lever arm away from the handle housing axially translates the rack within the handle housing.

5. The medical device of claim 4, wherein translation of the first portion of the lever arm away from the handle housing axially translates the rack proximally within the handle housing.

6. The medical device of claim 1, further comprising a locking element configured to prevent movement of the lever arm relative to the handle housing.

7. A medical device system, comprising:
- a stand configured to support at least one medical device; and
- a medical device securable to the stand, the medical device comprising:
  - an elongate shaft having a proximal end, a distal end, and a central longitudinal axis extending from the proximal end to the distal end;
  - a handle housing disposed at the proximal end of the elongate shaft; and
  - a cutting blade disposed proximate the distal end of the elongate shaft;
  - wherein a proximal portion of the handle housing includes an actuation mechanism including a lever arm having a first portion disposed outside of the handle housing and extending distally from the proximal portion of the handle housing;
  - wherein translation of the first portion of the lever arm relative to the handle housing axially translates the cutting blade within the elongate shaft; wherein the stand includes a second support member configured to engage a steering system having a steerable flexible tubular elongate member extending away from the second support member, the steering system being configured to receive the elongate shaft of the medical device within the steerable flexible tubular elongate member.

8. The medical device system of claim 7, wherein the stand includes a support member having a first yoke configured to engage the handle housing and a second yoke configured to engage the handle housing.

9. The medical device system of claim 8, wherein the handle housing includes a first groove configured to engage the first yoke and a second groove configured to engage the second yoke.

10. The medical device system of claim 8, wherein the support member includes at least one locking element configured to secure the handle housing to the support member.

11. The medical device system of claim 7, wherein the second support member includes a first yoke configured to engage a handle of the steering system and a second yoke configured to engage the handle of the steering system.

12. A medical device for cutting a suture during a minimally invasive procedure, comprising:
- an elongate shaft having a proximal end, a distal end, and a central longitudinal axis extending from the proximal end to the distal end;
- a handle housing disposed at the proximal end of the elongate shaft; and
- a cutting blade disposed proximate the distal end of the elongate shaft;
- wherein a proximal portion of the handle housing includes an actuation mechanism configured to translate the cutting blade within the elongate shaft;
- wherein the actuation mechanism includes:
- a rack disposed within the handle housing, wherein the rack is axially slidable parallel to the central longitudinal axis; and
- a lever arm having a first portion disposed outside of the handle housing and a second portion disposed inside of the handle housing, wherein the second portion includes a first leg fixedly attached to a first gear configured to engage the rack and a second leg fixedly attached to a second gear configured to engage the rack.

13. The medical device of claim 12, wherein translation of the first portion of the lever arm relative to the handle housing axially translates the rack within the handle housing.

14. The medical device of claim 12, wherein a pull wire extends from the rack to the cutting blade.

15. The medical device of claim 12, wherein the first leg and the second leg are disposed radially outward from the rack relative to the central longitudinal axis.

16. The medical device of claim 12, wherein the first leg and the second leg are disposed on opposite sides of the rack.

17. The medical device of claim 12, wherein a distal portion of the handle housing includes one or more ports in fluid communication with the elongate shaft.

* * * * *